(12) United States Patent
Makriyannis et al.

(10) Patent No.: US 8,202,893 B2
(45) Date of Patent: Jun. 19, 2012

(54) CANNABINERGIC LIPID LIGANDS

(75) Inventors: Alexandros Makriyannis, Watertown, MA (US); Chen Li, Storrs, CT (US); Dai Lu, Boston, MA (US)

(73) Assignee: University of Connecticut, Farmington, CT (US)

( * ) Notice: Subject to any disclaimer, the term of this patent is extended or adjusted under 35 U.S.C. 154(b) by 709 days.

(21) Appl. No.: 11/577,156

(22) PCT Filed: Oct. 12, 2005

(86) PCT No.: PCT/US2005/036524
§ 371 (c)(1),
(2), (4) Date: Feb. 27, 2009

(87) PCT Pub. No.: WO2006/044381
PCT Pub. Date: Apr. 27, 2006

(65) Prior Publication Data
US 2009/0163557 A1    Jun. 25, 2009

Related U.S. Application Data

(60) Provisional application No. 60/618,625, filed on Oct. 13, 2004.

(51) Int. Cl.
*A61K 31/44* (2006.01)
(52) U.S. Cl. ........ 514/352; 514/627; 514/371; 514/546; 514/560; 514/626; 554/224; 554/230

(58) Field of Classification Search .................. 514/352, 514/627, 371, 546, 560, 626; 554/224, 230
See application file for complete search history.

(56) References Cited

OTHER PUBLICATIONS

Vanrollins, M., Epoxygenase metabolites of docosahexaenoic and eicosapentaenoic acids inhibit platelet aggregation at concentrations below those affecting thromboxane synthesis; Journal of Pharmacology and Experimental Therapeutics, 274:798-804, 1995.*

* cited by examiner

*Primary Examiner* — Deborah D Carr
(74) *Attorney, Agent, or Firm* — Alix, Yale & Ristas, LLP

(57) ABSTRACT

One aspect of this disclosure relates generally to lipid compounds that exert diverse effects in the endocannabinoid system, such as regulating CB1 and CB2 receptor or moderating other bio-macromolecules within the endocannabinoid system. Some of the compounds showed improved receptor binding affinity, and/or improved receptor subtype selectivity, and improved bio-stability. Some of the compounds exhibit activities to regulate the enzymes that moderate the bio-disposal of endogenous cannabinoids, such as the fatty acid amide hydrolase (FAAH). Some of the compounds exhibit activities to inhibit the anandamide transporter. Other aspects of the invention are pharmaceutical preparations employing these ligands and methods of administering therapeutically effective amounts of the preparations to provide a physiological effect.

18 Claims, No Drawings

CANNABINERGIC LIPID LIGANDS

CROSS-REFERENCE TO RELATED APPLICATIONS

This application claims the benefit of U.S. Provisional Application No. 60/618,625 filed on Oct. 13, 2004, the contents of which are incorporated herein by reference in their entirety.

STATEMENT REGARDING FEDERALLY SPONSORED RESEARCH OR DEVELOPMENT

This invention was made with Government support under Grant No. DA7215 awarded by the National Institute on Drug Abuse. The Government may have certain rights in the invention.

This application is the U.S. National Phase of International Application Number PCT/US2005/036524 filed Oct. 12, 2005, which claims the benefit of U.S. Provisional Patent Application No. 06/618,625, filed Oct. 13, 2004, the contents of which are incorporated herein by reference in their entirety.

FIELD OF INVENTION

The present invention relates generally to fatty acid analogs and is more particularly concerned with lipid ligands that exert their effects in the endocannabinoid system, pharmaceutical preparations employing these analogs and methods of administering therapeutically effective amounts of the preparations to provide a physiological effect.

BACKGROUND

Cannabinoids, represented by (−)-$\Delta^9$-Tetrahydrocannabinol ($\Delta^9$-THC), are the active components of Cannabis Sativa, and known to exhibit behavioral and psychotropic effects, and possess therapeutic properties in a variety of areas such as the central nervous system, the cardiovascular system, the immune system and endocrine system.

Most of the effects of cannabinoids are due to interaction with specific high-affinity receptors. Presently, two cannabinoid receptors, CB1 and CB2, have been identified. Characterization of these receptors has been made possible by the development of specific synthetic ligands such as the agonists WIN 55212-2 (aminoalkyl indole) and CP 55,940 (non-classic cannabinoid).

The CB1 cannabinoid receptor has been primarily detected in the central nervous system (CNS) and to a lesser extent in certain peripheral tissues, such as, pituitary gland, immune cells, reproductive organs, gastrointestinal tissues, superior cervical ganglion, heart, lung, retina, urinary bladder and adrenal gland. The central distribution pattern of CB1 receptors accounts for several prominent pharmacological properties of cannabinoids, such as impairing cognition and memory and alternating the control of motor function, and mediating the psychotropic effects and other neurobehavioral effects of cannabinoids. Activation of CB1 receptor has been linked to a number of therapeutic indications seen in cannabinoids, such as analgesia, management of emesis, anxiety, feeding behavior, neuro-protection, movement disorder, glaucoma, cancer and cardiovascular diseases.

Conversely, the CB2 cannabinoid receptor does not appear to be expressed within the CNS but is primarily expressed within immune system. A high abundance of CB2 receptors have been detected in human tonsils, leukocytes, and spleen. In human leukocytes, CB2 receptors were found with particularly high concentration in B-cells, natural killer cells and macrophage. The high abundance of cannabinoid receptor CB2 subtype in the immune system suggest that the CB2 receptor could be the most likely cannabinoid receptor that mediates the immunomodulatory effects of cannabinoids. The immune modulatory effects of cannabinoids are very broad, including altering immune cell proliferation and function, altering antibody formation and altering cytokine production.

The discovery of cannabinoid receptors was followed by the identification of their endogenous ligands. So far, five of endogenous eicosanoids found in mammalian brain and certain other tissues have been identified to resemble the pharmacological activities of $\Delta^9$-THC and bind to the cannabinoid receptors. These endogenous cannabinergic eicosanoids include anandamide (arachidonoylethanolamide), 2-arachidonoylglycerol (2-AG), homo-γ-linolenoylethanolamide and docosatetraenoylethanolamide, and noladin ether. These compounds, collectively named as endocannabinoids, are synthesized by cells on demand, and released upon depolarization-induction. Endocannabinoids are generally produced by stimulus-dependent cleavage of membrane phospholipid precursors through two steps of enzymatic reactions: 1) generation of N-acyl-phosphatidylethanolamine (NAPE) via N-acylation of phosphatidylethanolamine (cephalin) by a N-acyltransferase, and 2) formation of N-acylethylamine from cleavage of NAPE by a N-acyl-phosphatidyl-ethanolamine-specific phospholipase D (NAPE-PLD). Of these endocannabinoids, the most investigated to date have been anandamide and 2-AG. There are indications that both anandamide and 2-AG can serve as neuromodulators or neurotransmitters.

In general, the endocannabinoids have been found to be somewhat less potent than $\Delta^9$-THC. Despite having a rapid onset of action, the magnitude and duration of action of these molecules are relatively short, presumably because of a rapid inactivation process, which is necessary to terminate their biological effects. The inactivation of anandamide appears to be a two-step process. It is first relocated from the extracellular side by carrier-facilitated reuptake and passive diffusion into cells, where it is then degraded by hydrolysis, catalyzed by the enzyme fatty-acid-amide-hydrolase (FAAH).

A high-affinity anandamide transporter has been characterized in rat cortical neurons and in astrocytes, but has not yet been isolated or cloned. This "anandamide transporter" appears to be a lipid uptake protein similar to, but distinct from, the prostaglandin uptake system. It was found that anandamide transport constitutes the rate-limiting step in the biological inactivation of anandamide, both in vitro and in vivo. Compound N-(4-hydroxyphenyl)-arachidonylamide (AM404) has been demonstrated to selectively and potently inhibit such transport, without binding to cannabinoid receptors or affecting anandamide-hydrolysis. Inhibitor AM404 was shown to enhance the receptor-mediated effects of anandamide, suggesting a potential for therapeutic intervention through transporter blockade.

Post reuptake, anandamide and 2-AG are disposed by a membrane-bound protein, fatty acid amide hydrolase (FAAH). FAAH was cloned in 1996. Its crystal structure was recently determined. FAAH is pH-dependent, selective and sensitive to an irreversible inhibitor PMSF (phenylmethylsulfonylfluoride).

Alternatively, an amidase, which is distinct from FAAH but also hydrolyzing anandamide and other N-acylethanolamines at acidic pH, was identified in human megakaryoblastic cells and rat organs such as lung and spleen. As for the 2-AG hydrolysis, in addition to the known monoacylglycerol (MAG) lipase, other esterases and FAAH may be involved. There are clear correspondences between brain levels of anandamide following pretreatment with FAAH inhibitors and pharmacological activity, which infer FAAH inhibitors as indirect sources for cannabinoid receptor activation.

It is also known that cyclo-oxygenase (COX) is the enzyme that catalyses the conversion of arachidonic acid to prostaglandins. To date, two isoforms are known, COX1 and COX2. COX1 is constitutively expressed in most tissues and COX2 is expressed in inflamed and neoplastic tissues. Experimental studies have shown that cyclo-oxygenase 2 (COX2) is involved in tumour development and progression. Hence, selective inhibitors of COX2 (coxibs) blocking tumour growth may be used as potential anticancer agents. In addition, inhibitors of COX2 also may be used as anti-inflammatory agents.

The CB1 and CB2 receptors, and the anandamide transporter as well as the enzymes involved in the biosynthesis, function and degradation of endocannabinoids have emerged as novel targets for therapeutic interventions. Two CB1 agonists, Marinol® and Cesamet®, have been marketed as controlled/non-controlled medications for treatment of anorexia seen in AIDS and cancer patients, and emesis associated with chemotherapy respectively. Currently, a CB1 inverse agonist (SR141716A) is in clinic trial for treatment of eating disorders. Although agonists of cannabinoid receptors exhibit a broad spectrum of pharmacological effects, the psychotropic properties of CB1 agonists have strongly limited the development of cannabinoid-based medications. A number of approaches have been taken to overcome these limitations, such as finding CB1 inverse agonists, CB2 selective agonists, water-soluble CB1/CB2 agonists, non-psychoactive cannabinoids, co-administration of CB1 agonists with other known medications as an effect-enhancer and agents indirect stimulating CB1 and CB2.

Synthetic analogues of the endocannabinoids commonly exhibit different functions to the endogenous cannabinoid system, including binding to the cannabinoid receptors CB1 and CB2 with enhanced affinity or bio-stability, inhibiting the enzyme FAAH or inhibiting the "anandamide transporter" as well as regulating the enzymes involved in bio-synthesis of endocannabinoids. These distinct features are rarely co-presented in one molecule. Inhibitors of FAAH, MAG lipase or anandamide transporter have the ability of indirectly stimulating the CB1 and CB2 receptors by maintaining or elevating de novo level of anandamide, therefore, serving as indirect agents to activate the cannabinoid receptors. Endocannabinoid analogues possessing the aforementioned features may exhibit fewer side effects than the ligands directly activating CB1 receptors, and provide novel therapeutic approaches to the disease states associated with the endocannabinoid system, such as pain, psychomotor disorders, multiple sclerosis, emesis, anxiety, feeding behaviors, glaucoma, neuro-degradation, cardiovascular disease and immune malfunction.

SUMMARY OF THE INVENTION

It has now been found that certain analogues of endogenous cannabinoids exhibit diverse effects on endocannabinoid system, such as regulating CB1 and CB2 receptor or moderating other bio-macromolecules within the endocannabinoid system. The invention covers novel analogues of endogenous cannabinoids, and their physiologically acceptable salts. Some of the inventive compounds showed improved receptor binding affinity, and/or improved receptor subtype selectivity, and improved bio-stability. Some of the inventive compounds exhibit activities to regulate the enzymes that moderate the bio-disposal of endogenous cannabinoids, such as the fatty acid amide hydrolase (FAAH). Some of the inventive compounds exhibit activities to inhibit the anandamide transporter. Although individual compound of this invention may vary in pharmacological properties, their structures can be represented by the general Formula I and Formula II, in which structural element FA represents the molecular backbone that consists of long chain hydrocarbons as later defined.

Formula I comprises:

$R_a$-FA-M-$R_b$

FA is a long chain hydrocarbon comprising 2 to 22 carbons and 0 to 6 double bonds. The double bonds can be conjugated or unconjugated. The FA long chain hydrocarbon is optionally substituted in any possible position with lower-alkyl, di-lower-alkyl, cycloalkyl or heterocycloalkyl groups. The FA long chain hydrocarbon may be interrupted with, or include, methylene, $(CH_3)_2C$, O, NH, N-alkyl, cyclic or heterocyclic groups and aryl.

M is X-Y-Z.

X is optionally present and if present comprises NH, N-lower alkyl, O, CH—

NHR where R comprises H, Boc or other group similar in size to Boc.

Y comprises C=O, C=S, C=NH, S=O, $SO_2$, $SO_3$, O=C—C=O or $CHNH_2$.

Z is optionally present and if present comprises O, NH, N-lower alkyl, $NQ_1Q_2$ wherein $Q_1$ and $Q_2$ each independently comprise H or alkyl, or $Q_1$ and $Q_2$ together comprises a phthalimido group or a part of a heterocyclic ring having 3 to about 7 ring members and optionally with one additional heteroatom selected from O, N, S.

$R_a$ comprises $E_1$-$X_1$-$E_2$-$T_1$ and $E_1$-$E_2$-$T_1$.

$E_1$ and $E_2$ are each independently alkyl, alkenyl or alkynyl having 0 to 10 carbons and optionally substituted with lower alkyl or di-lower-alkyl.

$X_1$ comprises NH, N-lower-alkyl and O.

$T_1$ comprises aryl, carbocyclic ring, bicyclic ring, tricyclic ring, heterocyclic ring, heterobicyclic ring, heterotricyclic ring, heteroaromatic ring, OH, SH, halogen, C(halogen)$_3$, CH(halogen)$_2$, O-alkyl, $N_3$, CN, NCS, $NH_2$, alkylamino, and dialkylamino or a substitutent group as defined later.

$R_b$ comprises —$(CH_2)_m$—$(C(CH_3)_2)_p$—$(CH_2)_n$-$T_2$-$T_3$, —$(CH_2)_m$—$(CH(CH_3))_q$—$(CH_2)_n$-$T_2$-$T_3$, where m and n are each an integer independently selected from 0 to 6; p and q are each an integer independently selected from 0 to 1.

$T_2$ is optionally present and if present comprises aryl, carbocyclic ring, bicyclic ring, tricyclic ring, heterocyclic ring, heterobicyclic ring, heterotricyclic ring heteroaromatic ring, 1- or 2-glycerol, 1- or 2-cyclic glycerol, alkyl, alkenyl, alkynyl;

$T_3$ comprises H, OH, SH, halogen, C(halogen)$_3$, CH(halogen)$_2$; O-alkyl, $N_3$, CN, NCS, $NH_2$, alkylamino, dialkylamino or a substitutent group as defined later.

In an advantageous variation FA is a long chain hydrocarbon comprising 12 to 22 carbons and 4 methylene-interrupted cis double bonds; and the X1 of $R_a$ comprises NH or N-lower alkyl.

In an advantageous variation FA is a long chain hydrocarbon comprising 12 to 22 carbons and 4 methylene-interrupted cis double bonds; and $R_a$ comprises $E_1$-$E_2$-$T_1$ wherein $T_1$ comprises aryl, heteroaromatic ring, cyclic ring, bicyclic ring, tricyclic ring, heterocyclic ring, hetero-bicyclic ring or a hetero-tricyclic ring.

In an advantageous variation FA is a long chain hydrocarbon comprising 12 to 22 carbons and 4 methylene-interrupted cis double bonds; and $R^a$ comprises $E_1$-$E_2$-$T_1$ wherein $T_1$ comprises OH, SH, halogen, C(halogen)$_3$, CH(halogen)$_2$, O-alkyl, $N_3$, CN, NCS, $NH_2$, alkylamino or dialkylamino.

Formula II comprises:

R-M-R'

R is a fatty acid tail remnant having 16 to 24 carbons or an alkyl-substituted fatty acid tail remnant having 16 to 24 carbons.

M is X-Y-Z, and

X is optionally present and comprises NH, N-lower alkyl, O and CH—NHR where R comprises H, Boc or other group similar in size to Boc. Y comprises C=O, C=S, C=NH, S=O, SO$_2$, SO$_3$, O=C—C=O or CHNH$_2$. Z is optionally present and comprises O, NH, N-lower alkyl, NQ$_1$Q$_2$ wherein Q$_1$ and Q$_2$ each independently comprise H or alkyl, or Q$_1$ and Q$_2$ together comprises a phthalimido group, or a part of a heterocyclic ring having 3 to about 7 ring members and optionally with one additional heteroatom selected from O, N, S.

R' comprises —(CH$_2$)$_m$—(C(CH$_3$)$_2$)$_p$—(CH$_2$)$_n$-T$_2$-T$_3$, —(CH$_2$)$_m$—(CH(CH$_3$))$_q$—(CH$_2$)$_n$-T$_2$-T$_3$, where m and n are each independently selected from 0 to 6 integer; and p or q is 0 or 1.

T$_2$ is optionally present and comprises aryl, carbocyclic ring, bicyclic ring, tricyclic ring, heterocyclic ring, heterobicyclic ring, heterotricyclic ring heteroaromatic ring, 1- or 2-glycerol, 1- or 2-cyclic glycerol, alkyl, alkenyl, alkynyl; T$_3$ comprises H, OH, SH, halogen, C(halogen)$_3$, CH(halogen)$_2$, O-alkyl, N$_3$, CN, NCS, NH$_2$, alkylamino, dialkylamino or other substation group defined later.

In variations of Formula II the following provisos apply:

When M is O—C(O)—NH and R is the tail remnant of arachidonyl acid, R' excludes ethyl, iso-propyl and propyl.

When M is NH—C(O)—NH and R is the tail remnant of arachidonyl acid, R' excludes methyl, iso-propyl, propyl, iso-butyl, CH$_2$CH$_2$F, CH$_2$CH$_2$OH, and CH2CH2OCH3.

When M is NH—C(O)—O and R is the tail remnant of arachidonyl acid, R' excludes ethyl, iso-propyl and CH$_2$CH$_2$F.

When M is NH—C(S)—NH and R is the tail remnant of arachidonyl acid, R' excludes 4-methyl-2-methoxy-phenol, and 4-methyl-2-chloro-phenol.

The inventive compounds include any and all possible isomers, stereoisomers and enantiomers. In general, the compositions of the invention may be alternately formulated to comprise, consist of, or consist essentially of, any appropriate components herein disclosed. The compositions of the invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

When the word "about" is used herein it is meant that the amount or condition it modifies can vary some beyond that so long as the advantages of the invention are realized. Practically, there is rarely the time or resources available to very precisely determine the limits of all the parameters of ones invention because to do would require an effort far greater than can be justified at the time the invention is being developed to a commercial reality. The skilled artisan understands this and expects that the disclosed results of the invention might extend, at least somewhat, beyond one or more of the limits disclosed. Later, having the benefit of the inventors disclosure and understanding the inventive concept and embodiments disclosed including the best mode known to the inventor, the inventor and others can, without inventive effort, explore beyond the limits disclosed to determine if the invention is realized beyond those limits and, when embodiments are found to be without any unexpected characteristics, those embodiments are within the meaning of the term about as used herein. It is not difficult for the artisan or others to determine whether such an embodiment is either as expected or, because of either a break in the continuity of results or one or more features that are significantly better than reported by the inventor, is surprising and thus an unobvious teaching leading to a further advance in the art.

A better understanding of the invention will be obtained from the following detailed description of the presently preferred, albeit illustrative, embodiments of the invention.

DETAILED DESCRIPTION OF THE INVENTION

Unless otherwise specifically defined, "acyl" refers to the general formula —C(O)alkyl.

Unless otherwise specifically defined, "acyloxy" refers to the general formula —O-acyl.

Unless otherwise specifically defined, "alcohol" refers to the general formula alkyl-OH and includes primary, secondary and tertiary variations.

Unless otherwise specifically defined, "alkyl" or "lower alkyl" refers to a linear, branched or cyclic alkyl group having from 1 to about 16 carbon atoms, and advantageously about 1 to about 6 carbon atoms, including, for example, methyl, ethyl, propyl, butyl, hexyl, octyl, isopropyl, isobutyl, tert-butyl, cyclopropyl, cyclohexyl, cyclooctyl, vinyl and allyl. Unless otherwise specifically defined, an alkyl group can be saturated or unsaturated. Unless otherwise specifically limited an alkyl group can be unsubstituted, singly substituted, or multiply substituted, with substituent groups in any possible position. Unless otherwise specifically limited, a cyclic alkyl group may include monocyclic, bicyclic, tricyclic, tetracyclic and polycyclic rings, for example norbornyl, adamantyl and related terpenes.

Unless otherwise specifically defined, "alkenyl" or "lower alkenyl" refers to a linear, branched or cyclic carbon chain having from 1 to about 16 carbon atoms, and advantageously about 1 to about 6 carbon atoms, and at least one double bond between carbon atoms in the chain. Examples include, for example, ethylene, allene, butene, butadiene, hexene, hexadiene, 5,5-dimethyl-1-hexene and cyclohexene. Unless otherwise specifically limited an alkenyl group can be unsubstituted, singly substituted, or multiply substituted, with substituent groups in any possible position.

Unless otherwise specifically defined, "alkoxy" refers to the general formula —O-alkyl.

Unless otherwise specifically defined, "alkylmercapto" refers to the general formula —S-alkyl.

Unless otherwise specifically defined, "alkylamino" refers to the general formula —(NH)-alkyl.

Unless otherwise specifically defined, "di-alkylamino" refers to the general formula —N-(alkyl)$_2$. Unless otherwise specifically limited di-alkylamino includes cyclic amine compounds such as piperidine and morpholine.

Unless otherwise specifically defined, "alkynyl" or "lower alkynyl" refers to a linear, branched or cyclic carbon chain having from 1 to about 16 carbon atoms, and advantageously about 1 to about 6 carbon atoms, and at least one triple bond between carbon atoms in the chain. Examples include, for example, ethyne, butyne, and hexyne. Unless otherwise specifically limited an alkynyl group can be unsubstituted, singly substituted, or multiply substituted, with substituent groups in any possible position.

Unless otherwise specifically defined, an aromatic ring is an unsaturated ring structure having about 5 to about 7 ring members and including only carbon as ring atoms. Unless otherwise specifically defined, an aromatic ring can be unsubstituted, singly substituted, or multiply substituted, with substituent groups in any possible position.

Unless otherwise specifically defined, "aryl" refers to an aromatic ring system that includes only carbon as ring atoms, for example phenyl, biphenyl or naphthyl. Unless otherwise specifically limited an aryl moiety can be unsubstituted, singly substituted, or multiply substituted, with substituent groups in any possible position.

Unless otherwise specifically defined, "aroyl" refers to the general formula —C(=O)-aryl.

Unless otherwise specifically defined, a bicyclic ring structure comprises 2 fused or bridged rings that include only carbon as ring atoms. The bicyclic ring structure may be saturated or unsaturated. Unless otherwise specifically limited a bicyclic ring structure can be unsubstituted, singly substituted, or multiply substituted, with substituent groups in any possible position. The individual rings may or may not be of the same type. Examples of bicyclic ring structures include, Dimethyl-bicyclo[3,1,1]heptane, bicyclo[2,2,1]heptadiene, decahydro-naphthalene and bicyclooctane.

Unless otherwise specifically defined, Bos is t-butoxycarbonyl, which has the general formula:

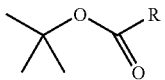

Unless otherwise specifically defined, a carbocyclic ring is a non-aromatic ring structure having about 3 to about 8 ring members, substituted or unsubstituted, that includes only carbon as ring atoms, for example, cyclohexadiene or cyclohexane. Unless otherwise specifically limited a carbocyclic ring structure can be unsubstituted, singly substituted, or multiply substituted, with substituent groups in any possible position.

Unless otherwise specifically defined, a cyclic glycerol includes members wherein 2 of the 3 hydroxy groups are tied to form a 5 to 8 member ring and the third hydroxyl group is substituted, for example in the form of an ester or an ether. The cyclic glycerol ring will typically, but not always, be saturated. The cyclic glycerol may be substituted in any possible position by one or more substituent groups. Examples of cyclic glycerols include

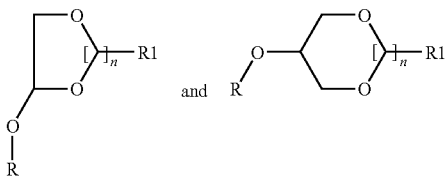

wherein n is an integer selected from 1 to 3.

Unless otherwise specifically defined, "halogen" refers to an atom selected from fluorine, chlorine, bromine and iodine.

Unless otherwise specifically defined, a heteroaromatic ring is an unsaturated ring structure having about 5 to about 8 ring members that have carbon atoms and one or more heteroatoms, including oxygen, nitrogen and/or sulfur, as ring atoms, for example, pyridine, furan, quinoline, and their derivatives. Unless otherwise specifically limited a heteroaromatic ring can be unsubstituted, singly substituted, or multiply substituted, with substituent groups in any possible position.

Unless otherwise specifically defined, a heterobicyclic ring structure comprises 2 fused or bridged rings that include carbon and one or more heteroatoms, including oxygen, nitrogen and/or sulfur, as ring atoms. The heterobicyclic ring structure is saturated or unsaturated. The heterobicyclic ring structure can be unsubstituted, singly substituted, or multiply substituted, with substituent groups in any possible position. The individual rings may or may not be of the same type. Examples of heterobicyclic ring structures include tropane, quinuclidine and tetrahydro-benzofuran.

Unless otherwise specifically defined, a heterocyclic ring is a saturated ring structure having about 3 to about 8 ring members that have carbon atoms and one or more heteroatoms, including oxygen, nitrogen and/or sulfur, as ring atoms, for example, piperidine, morpholine, piperazine, pyrrolidine, thiomorpholine, tetrahydropyridine, and their derivatives. The heterocyclic ring can be unsubstituted, singly substituted, or multiply substituted, with substituent groups in any possible position.

Unless otherwise specifically defined, a heterotricyclic ring structure comprises 3 rings that may be fused, bridged or both, and that include carbon and one or more heteroatoms, including oxygen, nitrogen and/or sulfur, as ring atoms. The heterotricyclic ring structure can be saturated or unsaturated. The heterotricyclic ring structure can be unsubstituted, singly substituted, or multiply substituted, with substituent groups in any possible position. The individual rings may or may not be of the same type. Examples of heterotricyclic ring structures include 2,4,10-trioxaadamantane, tetradecahydrophenanthroline.

Unless otherwise specifically defined, a heteropolycyclic ring structure comprises more than 3 rings that may be fused, bridged or both and that include carbon and one or more heteroatoms, including oxygen, nitrogen and/or sulfur, as ring atoms. The heteropolycyclic ring structure can be saturated or unsaturated. The heteropolycyclic ring structure can be unsubstituted, singly substituted or, if possible, multiply substituted, with substituent groups in any possible position. The individual rings may or may not be of the same type. Examples of heteropolycyclic ring structures include azaadamantine, 5-norbornene-2,3-dicarboximide.

Unless otherwise specifically defined, the term "phenacyl" refers to the general formula -phenyl-acyl.

Unless otherwise specifically defined, phthalimido has the general formula:

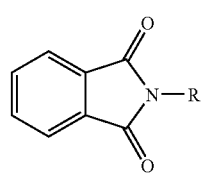

Unless otherwise specifically defined, a polycyclic ring structure comprises more than 3 rings that may be fused, bridged or both fused and bridged and that include carbon as ring atoms. The polycyclic ring structure can be saturated or unsaturated. Unless otherwise specifically limited a polycyclic ring structure can be unsubstituted, singly substituted, or multiply substituted, with substituent groups in any possible position. The individual rings may or may not be of the same type. Examples of polycyclic ring structures include adamantine, bicyclooctane, norbornane and bicyclononanes.

Unless otherwise specifically defined, a spirocycle refers to a ring system wherein a single atom is the only common member of two rings. A spirocycle can comprise a saturated carbocyclic ring comprising about 3 to about 8 ring members, a heterocyclic ring comprising about 3 to about 8 ring atoms wherein up to about 3 ring atoms may be N, S, or O or a combination thereof.

Unless otherwise specifically defined, a tricyclic ring structure comprises 3 rings that may be fused, bridged or both fused and bridged and that includes carbon as ring atoms. The tricyclic ring structure can be saturated or unsaturated. The tricyclic ring structure can be unsubstituted, singly substituted, or if possible, multiply substituted, with substituent groups in any possible position. The individual rings may or may not be of the same type. Examples of tricyclic ring structures include fluorene and anthracene.

Unless otherwise specifically defined, a fatty acid tail remnant is the hydrocarbon residue of the referenced fatty acid without the carboxyl head group.

Unless otherwise specifically limited the term substituted means substituted by at least one below described substituent group in any possible position or positions. Substituent groups for the above moieties useful in the invention are those groups that do not significantly diminish the biological activity of the inventive compound. Substituent groups that do not significantly diminish the biological activity of the inventive compound include, for example, H, halogen, $N_3$, NCS, CN, $NO_2$, $NX_1X_2$, $OX_3$, $C(X_3)_3$, OAC, O-acyl, O-aroyl, NH-acyl, NH-aroyl, NHCOalkyl, CHO, C(halogen)$_3$, $COOX_3$, $SO_3H$, $PO_3H_2$, $SO_2NX_1X_2$, $CONX_1X_2$, $COCF_3$, alkyl, alcohol, alkoxy, alkylmercapto, alkylamino, di-alkylamino, sulfonamide or thioalkoxy wherein $X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members and $X_3$ comprises H, alkyl, loweralkylhydroxy, or alkyl-$NX_1X_2$. Unless otherwise specifically limited, a substituent group may be in any possible position or any possible positions if multiply substituted.

As used herein a "therapeutically effective amount" of a compound, is the quantity of a compound which, when administered to an individual or animal, results in a sufficiently high level of that compound in the individual or animal to cause a discernible increase or decrease in stimulation of cannabinoid receptors. Physiological effects that result from cannabinoid receptor stimulation include analgesia, decreased nausea resulting from chemotherapy, sedation and increased appetite. Other physiological effects that result from cannabinoid receptor stimulation include relieving intraocular pressure in glaucoma patients and suppression of the immune system.

The compounds described herein, and physiologically acceptable salts thereof, have high potential when administered in therapeutically effective amounts for providing a physiological effect useful to treat pain; peripheral pain; glaucoma; epilepsy; nausea such as associated with cancer chemotherapy; AIDS Wasting Syndrome; cancer; neurodegenerative diseases including Multiple Sclerosis, Parkinson's Disease, Huntington's Chorea and Alzheimer's Disease; to enhance appetite; to reduce fertility; to prevent or reduce diseases associated with motor function such as Tourette's syndrome; to provide neuro-protection; to produce peripheral vasodilation and to suppress memory. Thus, another aspect of the invention is the administration of a therapeutically effective amount of an inventive compound, or a physiologically acceptable salt thereof, to an individual or animal to provide a physiological effect. Typically, a "therapeutically effective amount" of the compound ranges from about 10 mg/day to about 1,000 mg/day.

As used herein, an "individual" refers to a human. An "animal" refers to, for example, veterinary animals, such as dogs, cats, horses and the like, and farm animals, such as cows, pigs and the like.

The compound of the present invention can be administered by a variety of known methods, including orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular, subcutaneous ocular, intranasal, inhalation based or transdermal administration) and slow releasing microcarriers (for rectal, intramuscular or intravenous administration). The formulations can also contain a physiologically acceptable vehicle and optional adjuvants, flavorings, colorants and preservatives. Suitable physiologically acceptable vehicles may include, for example, saline, sterile water, Ringer's solution and isotonic sodium chloride solutions. The specific dosage level of active ingredient will depend upon a number of factors, including, for example, biological activity of the particular preparation, age, body weight, sex and general health of the individual being treated.

The following examples illustrated in Table 1 and Table 2 are given for purposes of illustration only in order that the present invention may be more fully understood. These examples are not intended to limit in any way the scope of the invention unless otherwise specifically indicated.

Some inventive analogs were tested for CB2 receptor binding affinity and for CB1 receptor affinity (to determine selectivity). As used herein, "binding affinity" is represented by the $K_i$ value which is the inhibition constant correlated with the concentration of an analog required to occupy the 50% of the total number (Bmax) of the receptors. The lower the $K_i$ value, the higher the binding affinity. As used herein an analog is said to have "binding selectivity" if it has higher binding affinity for one receptor compared to the other receptor; e.g. a cannabinoid analog which has an $K_i$ of 0.1 nM for CB2 and 10 nM for CB1, is 100 times more selective for the CB2 receptor. For the CB1 receptor binding studies, membranes were prepared from rat forebrain membranes according to the procedure of P. R. Dodd et al, *A Rapid Method for Preparing Synaptosomes: Comparison with Alternative Procedures*, Brain Res., 107-118 (1981). The binding of the novel analogues to the CB1 cannabinoid receptor was assessed as described in W. A. Devane et al, *Determination and Characterization of a Cannabinoid Receptor in a Rat Brain*, Mol. Pharmacol., 34, 605-613 (1988) and A. Charalambous et al, 5'-*azido* $\Delta^8$-*THC: A Novel Photoaffinity Label for the Cannabinoid Receptor*, J. Med. Chem., 35, 3076-3079 (1992) with the following changes. The above articles are incorporated by reference herein.

Membranes, previously frozen at −80° C., were thawed on ice. To the stirred suspension was added three volumes of TME (25 mM Tris-HCl buffer, 5 mM $MgCl_2$ and 1 mM EDTA) at a pH 7.4. The suspension was incubated at 4° C. for 30 min. At the end of the incubation, the membranes were pelleted and washed three times with TME.

The treated membranes were subsequently used in the binding assay described below. Approximately 30 µg of membranes were incubated in silanized 96-well microtiter plate with TME containing 0.1% essentially fatty acid-free bovine serum albumin (BSA), 0.8 nM [$^3$H] CP-55,940, and various concentrations of test materials in a final volume of 200 µL. The assays were incubated for 1 hour at 30° C. and then immediately filtered using Packard Filtermate 196 harvester and Whatman GF/C filterplates and washed with wash buffer (TME) containing 0.5% BSA. Radioactivity was detected using MicroScint 20 scintillation cocktail added directly to the dried filterplates, and the filterplates were counted using a Packard Instruments Top-Count. Nonspecific binding was assessed using 100 nM CP-55,940. Data collected from three independent experiments performed with duplicate determinations was normalized between 100% and 0% specific binding for [$^3$H] CP-55,940, determined using buffer and 100 nM CP-55,940. The normalized data was analyzed using a 4-parameter nonlinear logistic equation to yield $IC_{50}$ values. Data from at least two independent experiments performed in duplicate was used to calculate $IC_{50}$ values which were converted to $K_i$ values using the assumptions of Cheng et al, *Relationship Between the Inhibition Constant ($K_i$) and the concentration of Inhibitor which causes 50% Inhibition ($IC_{50}$) of an Enzymatic Reaction*, Biochem. Pharmacol., 22, 3099-3102, (1973), which is incorporated by reference herein.

For the CB2 receptor binding studies, membranes were prepared from frozen mouse spleen essentially according to the procedure of P. R. Dodd et al, *A Rapid Method for Preparing Synaptosomes: Comparison with Alternative Procedures*, Brain Res., 226, 107-118 (1981) which is incorporated by reference herein. Silanized centrifuge tubes were used throughout to minimize receptor loss due to adsorption. The CB2 binding assay was conducted in the same manner as for the CB1 binding assay. The binding affinities ($K_i$) were also expressed in nanomoles (nM).

Assay for FAAH Assay and Transporter Assay
FAAH Screening:

The FAAH (fatty acid amide hydrolase) enzyme preparation was obtained according to the procedure of Lang and Makriyannis et al *High Performance Liquid Chromatographic Determination of Anandamide Amidase Activity in Rat Brain Microsomes*, Analytical Biochemistry (238): 40-45, 1996.

All compound solutions were made to a concentration of 10 mM in DMSO. Three tests were performed on each compound: hydrolysis, to determine the stability of the compound in assay conditions without the enzyme present; metabolism, to determine the stability of the compound with the enzyme present; and inhibition of anandamide (native substrate) metabolism to arachidonic acid.

To test the stability of the compounds in enzyme assay conditions, 25 nmoles of the compound were incubated in TME buffer with 0.1% BSA (25 mM Tris base, 5 mM $MgCl_2$, 1 mM EDTA, pH 7.4; final volume of 250 µL) for 15 minutes at 37° C. Samples (100 µL) were taken at the start of the assay and after 15 minutes, diluted 1:5 with acetonitrile and centrifuged (20,000 RCF, five minutes, room temperature) to precipitate the proteins. The resulting supernatant was injected onto the HPLC. Calculations for determining the percent compound remaining are described in the following equation:

$$\% R = \text{Peak Area}(T15)/\text{Peak Area}(T0)$$

To determine whether or not the compounds were good substrates for FAAH, 25 nmoles of the compound were incubated with 75 µg enzyme preparation in TME buffer with 0.1% BSA (final volume 250 µL). The reaction mixture was treated in the same manner as described above. Concentrations of anandamide (AEA) and arachidonic acid (AA) were calculated using external standards. The rate of AA formation was calculated using the following equation:

$$\text{Rate}=(T15-T0)/15 \text{ min}/45 \text{ µg}$$

The inhibition of AEA metabolism was measured by mixing 25 nmoles of the compound with 25 nmoles AEA, and 75 µg enzyme preparation in TME buffer with 0.1% BSA (final volume of 250 µL). Again the reaction mixture was treated in the same manner as described above and the concentrations of AEA and AA were calculated using external standards. Percent inhibition was calculated using the following equation:

$$\% \text{ Inhib.}=(AA15-AA0)i/(AA15-AA0)s$$

where (AA15-AA0)c is the amount of arachidonic acid formed over 15 minutes from AEA with the inhibitor present and (AA15-AA0)s is the amount of arachidonic acid formed over 15 minutes from AEA when the inhibitor is not present. Compounds demonstrating greater than 40% inhibition were tested in the $IC_{50}$ studies where various concentrations of compound were incubated with 25 nmoles AEA, and 75 µg enzyme preparation in TME buffer (final volume of 250 µL). The reaction mixtures were treated as described above and the amount of AA formed was calculated. The software package GraphPad Prism was utilized to calculate $IC_{50}$ and $K_i$.

HPLC Conditions:

Chromatographic separation was achieved using an Ultrasphere ODS Pre-column (4.6×45 mm) from Beckman. Hardware consisted of a Waters Millennium HPLC system with a 20 µL injection loop. The mobile phase consisted of 8.5% o-phosphoric acid:acetonitrile (3:7), run isocratically at a rate of 1 mL/min and detection at 204 nm. The total run time was 8 minutes with AEA eluting at 2.2 minutes and AA at 6.0 minutes.

[$^3$H]Anandamide Transporter Competition Assay:

Human CCF-STG1 astrocytoma cells (American Type Culture collection) were grown in RPMI1640 culture medium containing 2 mM L-glutamine, 4.5 g/L glucose, 10 mM HEPES, and 1.0 mM sodium pyruvate, 10% FBS, cultures at 37° C. with 5% $CO_2$. For standard competition assays, confluent cells grown in 24-well plates were rinsed and pre-incubated for 10 min at 37° C. in assay buffer (Hank's Balanced Salt Solution containing 0.1% DMSO, 10 mM HEPES) plus test compounds (at their final concentrations of 0.01-100 µM). After having discarded the preincubation media, the cells were incubated for 4 min in 0.2 ml assay buffer containing 10 nM [$^3$H] anandamide (137.6 Ci/mmol, New England Nuclear) plus test compounds. Reactions were stopped by removing the incubation media and rinsing the cells three times with 0.5 ml of ice-cold HBSS buffer containing 0.1% fatty acid-free Bovine Serum Albumin (sigma). Radioactive material in Triton X-100 cell extracts was measured by liquid scintillation counting. A minimum of three independent experiments conducted in six replicates was used to define the concentration needed to produce half-maximal inhibition ($IC_{50}$) for each compound. $IC_{50}$ values were obtained by nonlinear regression fitting of the data, using the PRIZM software package. Data are expressed as mean±SEM.

Assay for Inhibition of MAG-Lipase

All compound solutions were made to a concentration of 10 mM in DMSO. Three tests were performed on each compound: hydrolysis, to determine the stability of the compound in assay conditions without the enzyme present; metabolism, to determine the stability of the compound with the enzyme present; and inhibition of 2-Arachidonoyl glycerol (native substrate) metabolism to arachidonic acid.

To test the stability of the compounds in enzyme assay conditions, 30 nmoles of the compound were incubated in TME buffer (25 mM Tris base, 5 mM $MgCl_2$, 1 mM EDTA, pH 7.4; final volume of 300 μL) for 20 minutes at 37° C. Samples (100 μL) were taken at the start of the assay and after 20 minutes, diluted 1:5 with acetonitrile and centrifuged (20,000 RCF, five minutes, room temperature) to precipitate the proteins. The resulting supernatant was injected onto the HPLC. Calculations for determining the percent compound remaining are described in the following equation:

$$\% R = \text{Peak Area}(T_{20})/\text{Peak Area}(T_0)$$

To determine whether or not the compounds were good substrates for Mag-lipase, 30 nmoles of the compound were incubated with 30 μg enzyme preparation (supernatant from final spin in the anandamide amidase preparation) in TME buffer (final volume 300 μL). The reaction mixture was treated in the same manner as described above. Concentrations of 2-Arachidonoyl glycerol (2-AG) and arachidonic acid (AA) were calculated using external standards. The rate of AA formation was calculated using the following equation:

$$\text{Rate} = (T_{20}-T_0)/20 \text{ min}/10 \text{ μg}$$

The inhibition of 2-AG metabolism was measured by mixing 30 nmoles of the compound with 30 nmoles 2-AG, and 30 μg enzyme preparation in TME buffer (final volume of 300 μL). Again the reaction mixture was treated in the same manner as described above and the concentrations of 2-AG and AA were calculated using external standards. Percent inhibition was calculated using the following equation:

$$\% \text{ Inhib.} = (AA_{20}-AA_0)i/(AA_{20}-AA_0)s$$

where $(AA_{20}-AA_0)i$ is the amount of arachidonic acid formed over 20 minutes from 2-AG with the inhibitor present and $(AA_{20}-AA_0)s$ is the amount of arachidonic acid formed over 20 minutes from 2-AG when the inhibitor is not present. Compounds demonstrating greater than 40% inhibition were tested in the $IC_{50}$ studies where various concentrations of compound were incubated with 30 nmoles 2-AG, and 30 μg enzyme preparation in TME buffer (final volume of 300 μL). The reaction mixtures were treated as described above and the amount of AA formed was calculated. The software package GraphPad Prism was utilized to calculate $IC_{50}$ and $K_i$.

HPLC Conditions:

Chromatographic separation was achieved using an Ultrasphere ODS Pre-column (4.6×45 mm) from Beckman. Hardware consisted of a Waters Millennium HPLC system with a 20 μL injection loop. The mobile phase consisted of 8.5% o-phosphoric acid:acetonitrile (3:7), run isocratically at a rate of 1 mL/min and detection at 204 nm. The total run time was 8 minutes with 2-AG eluting at 3.0 minutes and AA at 6.0 minutes.

Assay for Inhibition of COX:

All compound solutions were made to a concentration of 10 mM in DMSO. Three tests were performed on each compound: hydrolysis, to determine the stability of the compound in assay conditions without the enzyme present; metabolism, to determine the stability of the compound with the enzyme present; and inhibition of arachidonic acid (AA) metabolism.

To test the stability of the compounds in enzyme assay conditions, 25 nmoles of the compound were incubated with 12.5 μl 100 uM hematin in assay buffer (0.1M PH8.0 Tris-HCl, 2 mM phenol, 5 mM EDTA, 0.1% BSA, final volume of 250 μL) for 2 minutes at 25° C. Samples (100 μL) were taken at the start of the assay and after 2 minutes, diluted 1:5 with acetonitrile and centrifuged (20,000 RCF, five minutes, room temperature) to precipitate the proteins. The resulting supernatant was injected onto the HPLC. Calculations for determining the percent compound remaining are described in the following equation:

$$\% R = \text{Peak Area}(T_2)/\text{Peak Area}(T_0)$$

To determine whether or not the compounds were good substrates for COX enzyme, 25 nmoles of the compound were incubated with 12.5 μl COX enzyme (purchased form Cayman Chemical) and 5 uM hematin in assay buffer (final volume 250 μL). The reaction mixture was treated in the same manner as described above. Concentrations of AA were calculated using external standards. The rate of AA metabolism was calculated using the following equation:

$$\text{Rate} = (T_0-T_2)/2 \text{ min}/5 \text{ ul}$$

The inhibition of AA metabolism was measured by mixing 25 nmoles of the compound with 25 nmoles AA, and 12.5 μl COX enzyme (purchased form Cayman Chemical) with 5 μM hematin in assay buffer (final volume 250 μL). Again the reaction mixture was treated in the same manner as described above and the concentrations of AA were calculated using external standards. Percent inhibition was calculated using the following equation:

$$\% \text{ Inhib.} = (AA_0-AA_2)i/(AA_0-AA_2)s$$

where $(AA_0-AA_2)i$ is the amount of arachidonic acid metabolized over 2 minutes with the inhibitor present and $(AA_0-AA_2)s$ is the amount of arachidonic acid metabolized over 2 minutes when the inhibitor is not present. Compounds demonstrating greater than 40% inhibition were tested in the $IC_{50}$ studies where various concentrations of compound were incubated with 25 nmoles AA, and 12.5 μl COX enzyme (purchased form Cayman Chemical) with 5 μM hematin in assay buffer (final volume 250 μL). The reaction mixtures were treated as described above and the amount of AA metabolized was calculated. The software package GraphPad Prism was utilized to calculate $IC_{50}$ and $K_i$.

HPLC Conditions:

Chromatographic separation was achieved using an Ultrasphere ODS Pre-column (4.6×45 mm) from Beckman. Hardware consisted of a Waters Millennium HPLC system with a 20 μL injection loop. The mobile phase consisted of 8.5% o-phosphoric acid:acetonitrile (3:7), run isocratically at a rate of 1 mL/min and detection at 204 nm. The total run time was 8 minutes with AA at 6.0 minutes.

Synthesis Scheme and Experimental Details

Synthetic Route for General Intermediate of Anandamide Analogues (M7):

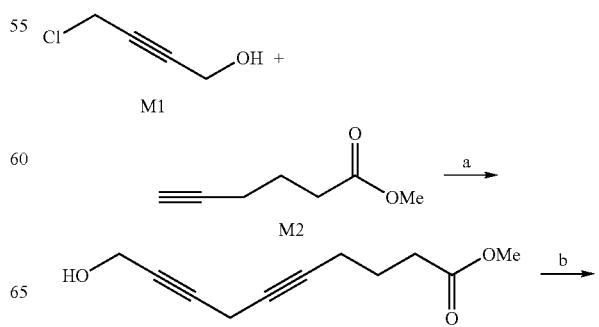

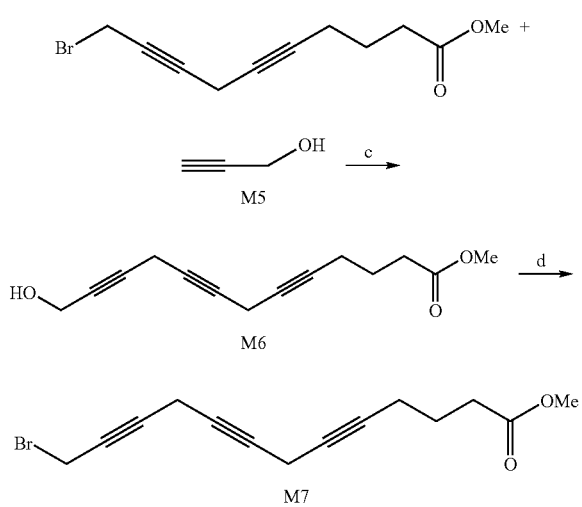

Reagents and conditions:
a. CuI, NaI, K₂CO₃, DMF, rt, 85%;
b. PPh₃, CBr₄, 0° C., 85%;
c. CuI, NaI, K₂CO₃, DMF, rt, 80%;
d. PPh₃, CBr₄, 0° C., 82%.

Compound M3:

The 4-chlorobut-2-ny-1-ol (M1) (28.7 mmol) and Hex-5-ynoic acid methyl ester (M2) (28.7 mmol) were added to a suspension of the salt of CuI (57.4 mmol), NaI (57.4 mmol) and K₂CO₃ (43 mmol) in 10 mL of anhydrous DMF under Ar. The mixture was stirred overnight at r.t., the reaction was quenched with sat. NH₄Cl and the lipophilic products were extracted with Et₂O. The combined organic extracts were washed with water and brine, dried with Na₂SO₄. After rotary evaporation of solvents, the residue was chromatographed on silica gel to afford 24.4 mmol (85% yield) of pure title compound M3.

Compound M4:

A solution of PPh₃ (26.8 mmol) in 15 mL of dry CH₂Cl₂ was added dropwise to a stirred solution of the M3 (24.4 mmol) and CBr₄ (26.8 mmol) in 15 mL of dry CH₂Cl₂ at 0° C. Then, the mixture was stirred for another 1.5 h at 0° C. The solvent was evaporated and the residue was diluted in Et₂O and filtered through a short pad of celite. The filtrate was concentrated and was purified on silica gel column chromatography to provide 20.7 mmol (85% yield) of M4 as an oil.

Compound M6:

The compound M6 was synthesized by coupling M4 (20.7 mmol) with prop-2-yn-1-ol (M5) (24.9 mmol) following the procedure described for compound M3 to give 16.6 mmol (80% yield) of 13-hydroxyl-tirdeca-5,8,11-triynoic acid methyl ester (M6) as a pale-yellow oil.

Compound M7:

The compound M7 was prepared from compound M6 (16.6 mmol) and CBr₄ (18.3 mmol) following the procedure described for compound M4 to afford 13.6 mmol (82% yield) of title compound M7 as a pale-yellow oil.

Preparation of Compounds A1-A4:

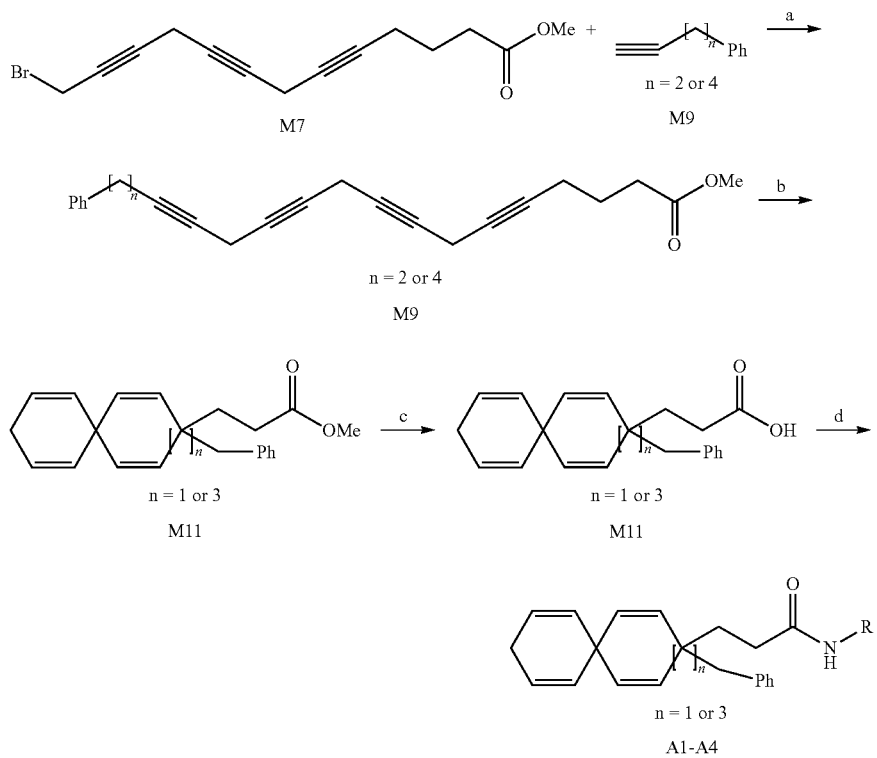

Reagents and conditions:
a. a. CuI, NaI, K₂CO₃, DMF, rt, 85%;
b. H₂, Lindlar's catalyst, Et₂O/THF, r.t.;
c. 1 M LiOH, THF, r.t.;
d. oxalyl chloride/DMF, cyclopropyl amine, CH₂Cl₂, 0° C.-r.t.

Compound M10

The compound M10 was synthesized by coupling M7 (10 mmol) with respective alkyl (M9) (12 mmol) following the procedure described for compound M3 to give 8 mmol (80% yield) of M10 as a pale-yellow oil.

Compound M11:

To a 250 mL flask containing 1.5 g of Lindlar's catalyst was added 20 mL of $Et_2O$. The mixture was saturated with $H_2$ at r.t. and a solution of M10 (1 g) in 15 mL of THF and quinoline (200 mg) were added under a stream of $H_2$. The reaction was monitored by $^1H$ NMR. After the hydrogenation was finished, the mixture was filtered, washed by 2N aqueous HCl and brine and dried by $Na_2SO_4$. The solvent was evaporated, and the residue was chromatographed on silica gel to afford 0.77 g (75% yield) of M11 as colorless oil.

Compound M12:

To a solution of compound M11 (2.1 mmol) in 10 mL of THF was added 1M LiOH (5.6 mL) at r.t. under Ar. Stirring was continued further for 48 h. The reaction mixture was acidified with 2N HCl to pH 5.5 and lipophilic products were extracted by $Et_2O$. The combined organic extract was washed water and brine, dried by $Na_2SO_4$. The solvent was evaporated in vacuo to give a yellowish oily residue. Chromatography on silica gel afforded M12 (1.68 mmol, 80% yield) as a colorless oil.

Compound A1-A4:

To a solution of acid M12 (0.1 mmol) and DMF (0.01 mL) in 5 mL of $CH_2Cl_2$ at 0° C. was added of oxalyl chloride (0.1 mL, 0.2 mmol) in a dropwise manner, The reaction mixture was stirred further at 0° C. for an additional 1.5 h. Then 1.0 mmol of respective amine was added to above mixture very slowly at 0° C. Stirring was continued further for overnight at ambient temperature. It was diluted by $Et_2O$, washed by water and brine and dried over $Na_2SO_4$. The solvent was removed in vacuo to give crude product. Chromatography on silica gel afforded A1-A4 (70-90% yield) as an oil.

Preparation of Compounds A5-A16:

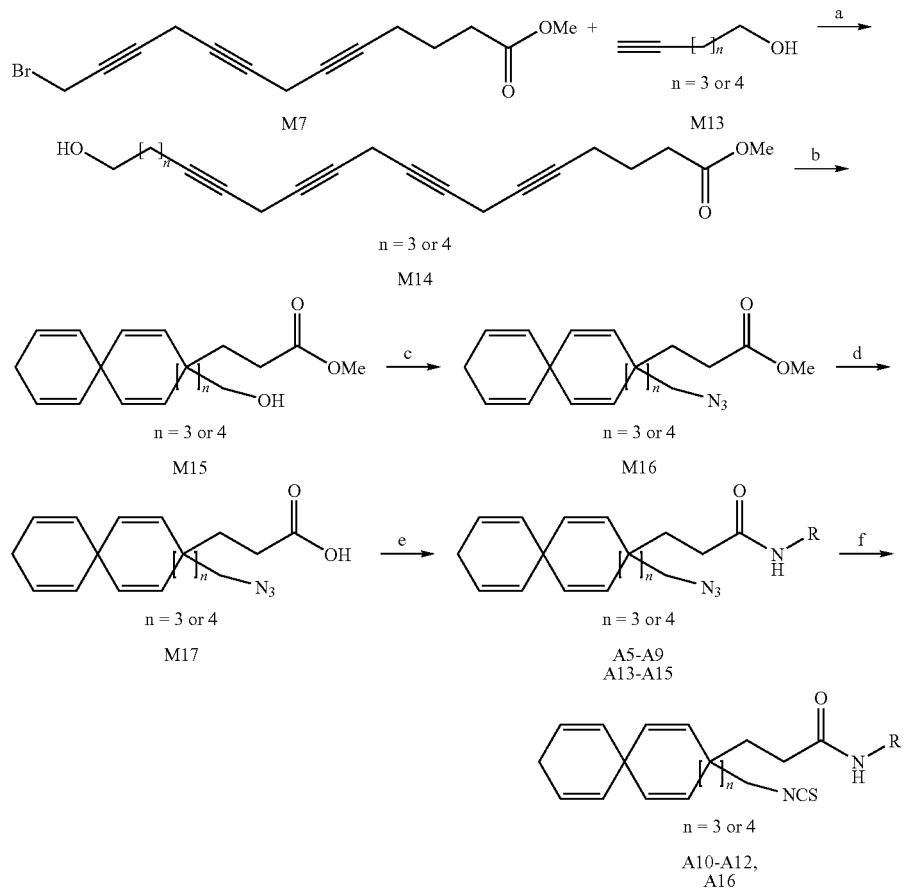

Reagents and conditions:
a. CuI, NaI, $K_2CO_3$, DMF, rt, 85%;
b. $H_2$, Lindlar's catalyst, $Et_2O$/THF, r.t.
c. $Zn(N_3)_2 \cdot 2Py$, DIAD, $PPh_3$, toluene, 0° C.-r.t., 87%;
d. 1 M LiOH, THF, r.t., 80%;
e. oxalyl chloride/DMF, cyclopropyl amine, $CH_2Cl_2$, 0° C.-r.t., 90%;
f. $CS_2$, $PPh_3$, THF, 80%.

Compound M14:

The compound M14 was synthesized by coupling M7 (13.6 mmol) with M13 (16.3 mmol) following the procedure described for compound M3 to give M18 (11.6 mmol, 85% yield) as a pale-yellow oil.

Compound M15:

To a 250 mL flask containing 5.67 g of Lindlar's catalyst was added 20 mL of $Et_2O$. The mixture was saturated with $H_2$ at r.t. and a solution of M15 (11.6 mmol) in 15 mL of THF and quinoline (300 mg) were added under a stream of $H_2$. The reaction was monitored by $^1$H NMR. After the hydrogenation was finished, the mixture was filtered, washed by 2N HCl and brine and dried by $Na_2SO_4$. The solvent was evaporated, and the residue was chromatographed on silica gel to afford 9.6 mmol (83% yield) of M15 as a colorless oil.

Compound M16:

$ZnN_6$.2Py (7.7 mmol) was suspended in a solution of the 20-hydroxy-icos-5,8,11,14-tetraenoic acid methyl ester M15 (9.6 mmol) and $PPh_3$ (19.2 mmol) in 20 mL of anhydrous toluene. To this stirred mixture at r.t. diisopropyl azodicarboxylate (19.2 mmol) was added dropwise. Stirring was continued until complete consumption (TLC monitoring) of M15 was observed. The heterogeneous mixture was filtered over a Celite pad, concentrated in vacuo and purified by column chromatography to afford the pure M16 (8.4 mmol, 87% yield) as a colorless oil.

Compound M17:

To a solution of compound M16 (2.8 mmol) in 10 mL of THF was added 1M LiOH (5.6 mL) at r.t. under Ar. Stirring was continued further for 48 h. The reaction mixture was acidified with 2N HCl to pH 5.5 and lipophilic products were extracted by $Et_2O$. The combined organic extract was washed water and brine, dried by $Na_2SO_4$. The solvent was evaporated in vacuo to give a yellowish oily residue. Chromatography on silica gel afforded M17 (2.24 mmol, 80% yield) as a colorless oil.

Compound A5-A9, A13-A15:

To a solution of acid M24 (0.29 mmol) and DMF (0.02 mL) in 5 mL of $CH_2Cl_2$ at 0° C. was added of oxalyl chloride (0.29 mL, 0.58 mmol) in a dropwise manner, The reaction mixture was stirred further at 0° C. for an additional 1.5 h. Then 2.9 mmol of respective amine was added to above mixture very slowly at 0° C. Stirring was continued further for overnight at ambient temperature. It was diluted by $Et_2O$, washed by water and brine and dried over $Na_2SO_4$. The solvent was removed in vacuo to give crude product. Chromatography on silica gel afforded A5-A9 and A13-A15 (70-90% yield) as an oil.

Compound A10-A12 and A16:

To a solution of respective azide compounds (0.13 mmol) in 2 mL of anhydrous THF were added $PPh_3$ (0.2 mmol) in a single portion at room temperature. Then, carbon disulfide (1.3 mmol) was added to above reaction mixture. The reaction mixture was stirred at r.t. for 48 h and was subsequently concentrated in vacuo. The residue was purified by column chromatography to afford pure A10-A12 and A16 (60-80% yield) as oil.

Preparation of A17-A20:

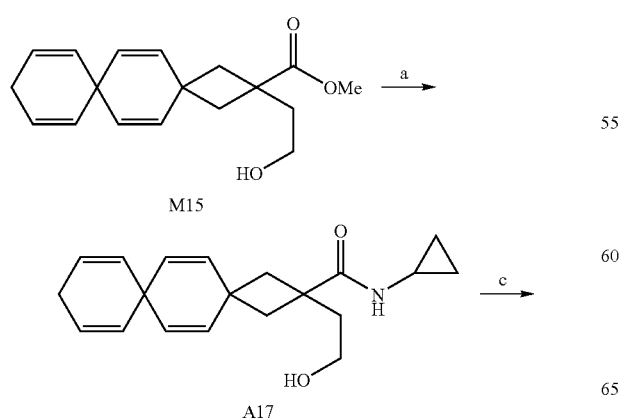

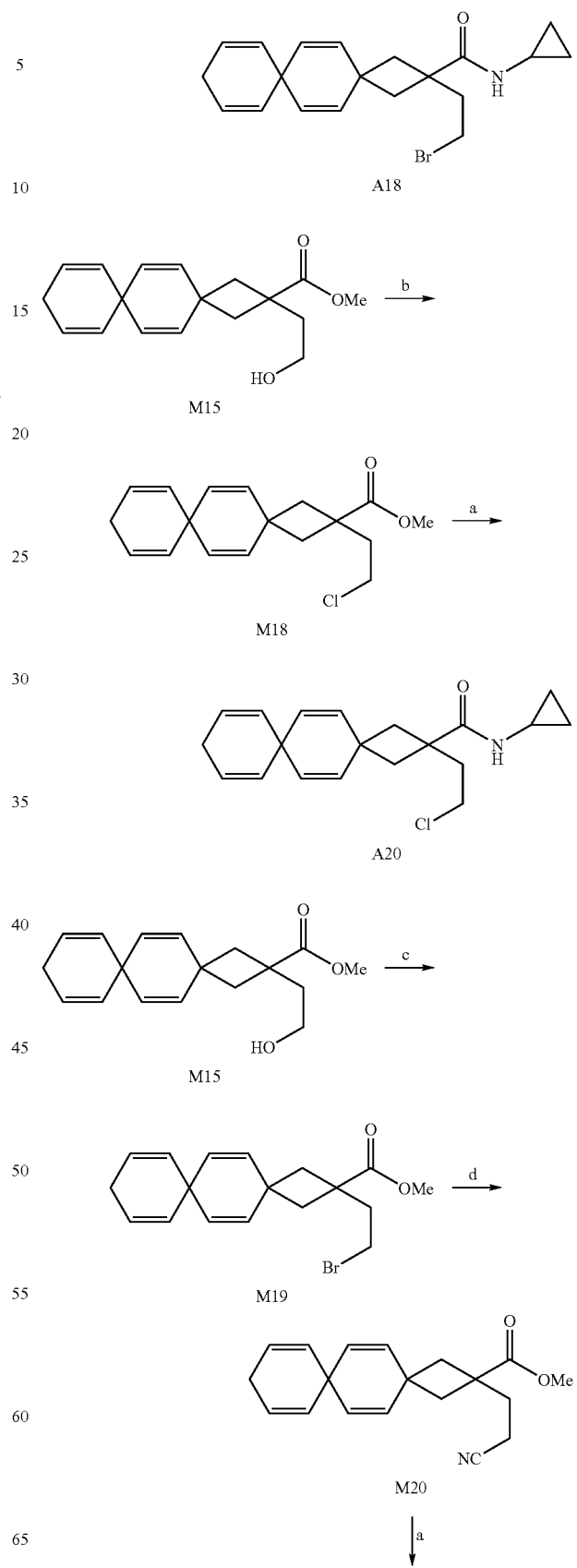

-continued

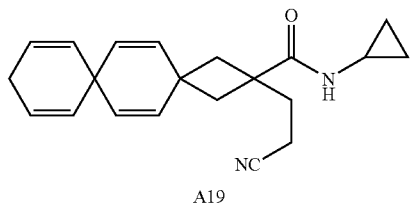

A19

Reagents and conditions:
a. AlCl₃, CH₂Cl₂, amines, 70-85%;
b. PPh₃, CCl₄, r.t., 85%;
c. PPh₃, CBr₄, 0° C., 80-85%;
d. TBAF, TMSCN, THF, r.t. 80%.

Compound A17:

To a suspension of AlCl₃ (5 mmol) in 2 mL anhydrous CH₂Cl₂ was added respective amine (6 mmol) in a dropwise manner at 0° C. After 10 min, a solution of M15 (0.5 mmol) in 1 mL anhydrous CH₂Cl₂ was adder to above suspension. Stirring was continued for overnight. Then, it was diluted with Et₂O, and heterogeneous mixture was filtered through a pad of Celite. The filtrate was concentrated in vacuo, and purified by chromatograph on silica gel to afford pure A17 (0.4 mmol, 80% yield) as oil.

Compound A18:

A solution of PPh₃ (0.22 mmol) in 1.5 mL of dry CH₂Cl₂ was added dropwise to a stirred solution of the A17 (0.2 mmol) and CBr₄ (0.22 mmol) in 1.5 mL of dry CH₂Cl₂ at 0° C. Then, the mixture was stirred for another 1.5 h at 0° C. The solvent was evaporated and the residue was diluted in Et₂O and filtered through a short pad of celite. The filtrate was concentrated and purified on silica gel column chromatography to provide A18 (0.16 mmol, 80%) as oil.

Compound M18:

A solution of PPh₃ (0.60 mmol) in 3 mL of dry CH₂Cl₂ was added dropwise to a stirred solution of the M15 (0.5 mmol) and CCl₄ (1.0 mmol) in 1.5 mL of dry CH₂Cl₂ at 0° C. Then, the mixture was stirred for another 24 h at ambient temperature. The solvent was evaporated and the residue was diluted in Et₂O and filtered through a short pad of celite. The filtrate was concentrated and purified on silica gel column chromatography to provide M18 (0.43 mmol, 85%) as oil.

Compound A20:

To a suspension of AlCl₃ (4 mmol) in 2 mL anhydrous CH₂Cl₂ was added respective amine (4.8 mmol) in a dropwise manner at 0° C. After 10 min, a solution of M18 (0.4 mmol) in 1 mL anhydrous CH₂Cl₂ was adder to above suspension. Stirring was continued for overnight. Then, it was diluted with Et₂O, and heterogeneous mixture was filtered through a pad of Celite. The filtrate was concentrated in vacuo, and purified by chromatograph on silica gel to afford pure A20 (0.34 mmol, 85% yield) as oil.

Compound M19:

A solution of PPh₃ (1.2 mmol) in 3 mL of dry CH₂Cl₂ was added dropwise to a stirred solution of the M15 (1 mmol) and CBr₄ (1.2 mmol) in 2 mL of dry CH₂Cl₂ at 0° C. Then, the mixture was stirred for another 2 h at 0° C. The solvent was evaporated and the residue was diluted in Et₂O and filtered through a short pad of celite. The filtrate was concentrated and purified on silica gel column chromatography to provide M19 (0.85 mmol, 85%) as oil.

Compound M20:

To a solution of M19 (0.85 mmol) in 2 mL of anhydrous THF was added TMSCN (1.3 mmol) at room temperature. Then, 1.3 mL of TBAF in THF (1 M) was added to above reaction mixture in a dropwise manner. Stirring was continued overnight. The reaction was quenched by MeOH, and the solvent was removed in vacuo. The reaction mixture was re-dissolved in Et₂O, and washed with water and brine, dried over Na₂SO₄, concentrated in vacuo. The residue was chromatographed on silica gel to give pure M20 (0.68 mmol, 80% yield) as oil.

Compound A19:

To a suspension of AlCl₃ (5 mmol) in 2 L anhydrous CH₂Cl₂ was added respective amine (6 mmol) in a dropwise manner at 0° C. After 10 min, a solution of M20 (0.5 mmol) in 1 mL anhydrous CH₂Cl₂ was adder to above suspension. Stirring was continued for overnight. Then, it was diluted with Et₂O, and heterogeneous mixture was filtered through a pad of Celite. The filtrate was concentrated in vacuo, and purified by chromatograph on silica gel to afford pure A19 (0.35 mmol, 70% yield) as oil.

Preparation of A21:

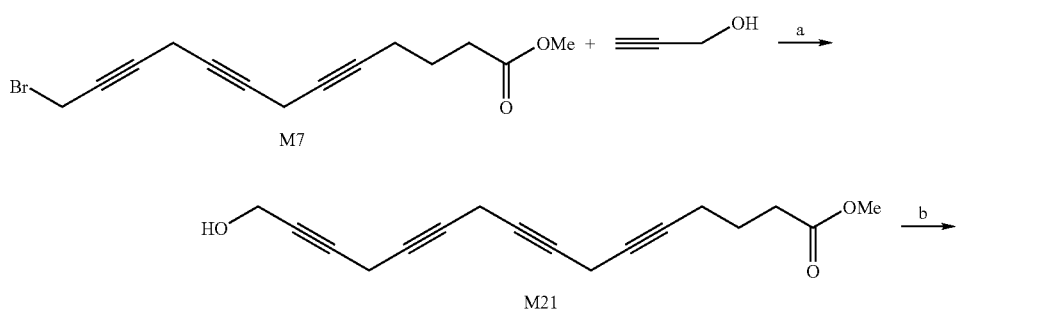

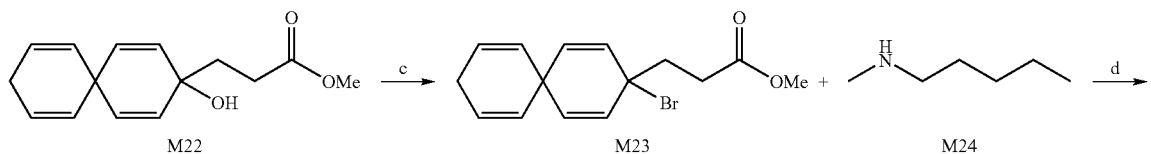

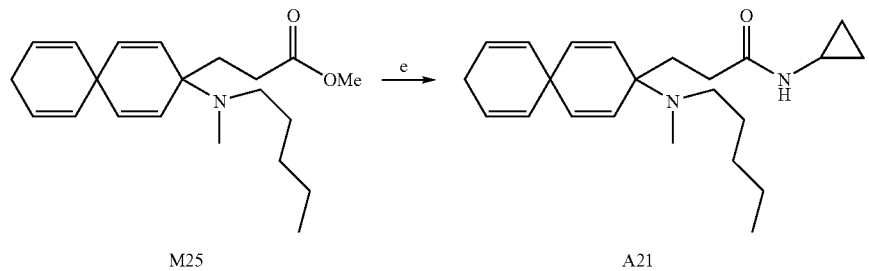

Reagents and conditions:
a. CuI, NaI, K$_2$CO$_3$, DMF, rt, 85%;
b. H$_2$, Lindlar's catalyst, Et$_2$O/THF, r.t.;
c. PPh$_3$, CBr$_4$, 0° C., 85%;
d. K$_2$CO$_3$, DMF, 70° C., 66%;
e. AlCl$_3$, CH$_2$Cl$_2$, amines, 70-90%.

Compound M21:

The compound M21 was synthesized by coupling M7 (10 mmol) with prop-2-yn-1-ol (M5) (12 mmol) following the procedure described for compound M3 to give 3.8 g (8 mmol, 80% yield) of M21 as a pale-yellow oil.

Compound M22:

To a 250 mL flask containing 3.24 g of Lindlar's catalyst was added 20 mL of Et$_2$O. The mixture was saturated with H$_2$ at r.t. and a solution of M21 (2.16 g, 8 mmol) in 15 mL of THF and quinoline (100 mg) were added under a stream of H$_2$. The reaction was monitored by $^1$H NMR. After the hydrogenation was finished, the mixture was filtered, washed by 2N HCl and brine and dried by Na$_2$SO$_4$. The solvent was evaporated, and the residue was chromatographed on silica gel to afford 1.85 g (6.64 mmol, 83% yield) of M22 as colorless oil.

Compound M23:

The compound M23 was prepared from compound M22 (6.64 mmol) and CBr$_4$ (7.3 mmol) following the procedure described for compound M4 to afford (5.44 mmol, 82% yield) title compound M23 as a pale-yellow oil.

Compound M25:

To a suspension of K$_2$CO$_3$ (2.65 mmol) and compound M23 (0.89 mmol) in 3.5 mL anhydrous DMF was added methyl-pentyl-amine (M24) (0.979 mmol) at room temperature. The reaction mixture was heated to 80° C. and stirred for another 12 h. Then, it was cooled to room temperature, diluted with Et$_2$O, wash with water and brine, dried over Na$_2$SO$_4$. The solvent was evaporated, and the residue was chromatographed on silica gel to afford pure M25 (0.6 mmol, 67% yield) as oil.

Compound A21:

To a suspension of AlCl$_3$ (5 mmol) in 2 mL anhydrous CH$_2$Cl$_2$ was added cyclopropylamine (6 mmol) in a dropwise manner at 0° C. After 10 min, a solution of M25 (0.5 mmol) in 1 mL anhydrous CH$_2$Cl$_2$ was adder to above suspension. Stirring was continued for overnight. Then, it was diluted with Et$_2$O, and heterogeneous mixture was filtered through a pad of Celite. The filtrate was concentrated in vacuo, and purified by chromatograph on silica gel to afford pure A21 (75% yield) as oil.

Preparation of Compound A22-A27:

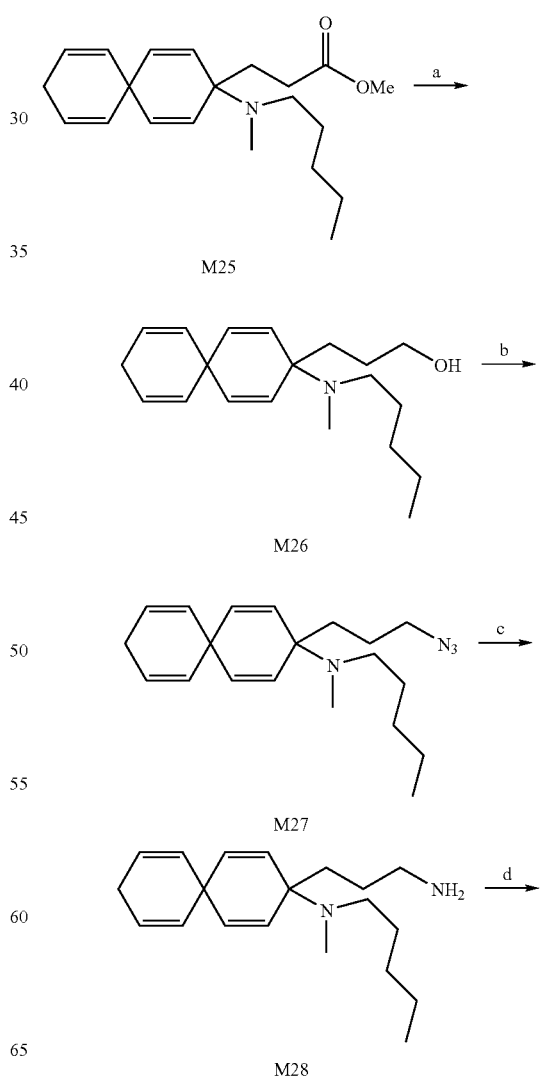

-continued

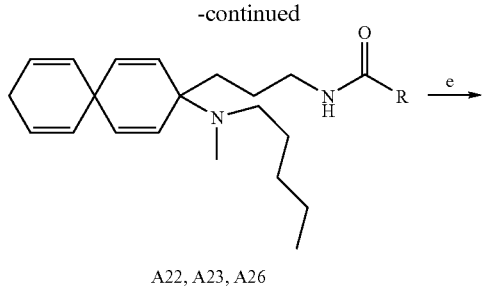

A22, A23, A26

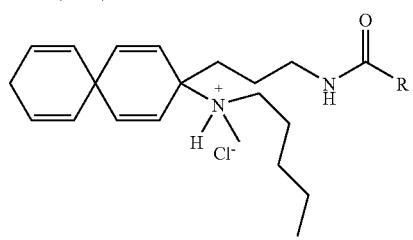

A24, A25, A27

Reagents and conditions:
a. H₄LiAl, Et₂O, 95%;
b. Zn(N₃)₂•2Py, DIAD, PPh₃, toluene, 0° C.-r.t., 87%;
c. H₄LiAl, Et₂O, 88%;
d. CH₂Cl₂, acid chloride, Et₃N, 85-90%;
e. HCl•Et₂O, Et₂O, r.t.

Celite pad, concentrated in vacuo and purified by column chromatography to afford the pure M27 (0.78 mmol, 82% yield) as oil.

Compound M28:

To a solution of M27 (0.78 mmol) in 3 mL anhydrous Et₂O was added 1.3 mL of 1M H₄AlLi in Et₂O at 0° C. Stirring was continued for overnight at ambient temperature. The reaction was quenched by 0.05 mL water, 0.05 mmol 15% NaOH and 0.15 mmol water, respectively. The heterogeneous mixture was filtered through a pad of Celite, concentrated in vacuo to give pure M28 (0.62 mmol, 80% yield) as oil.

Compound A22-A23 and A26:

To a solution of M28 (0.2 mmol) and Et₃N (1.6 mmol) in 1 mL of anhydrous CH₂Cl₂ was added respective acid chloride (0.25 mmol) at 0° C. Stirring was continued for another 5 h at ambient temperature. Then, the reaction mixture was diluted with Et₂O, washed with water and brine, dried over Na₂SO₄. The solvent was removed in vacuo, and residue was purified by chromatograph on silica gel to afford final compound A22-A23 and A26 (75-90% yield).

Compound A24-A25 and A27:

To a solution of A22, A23 and A26 (0.1 mmol) in 0.5 mL of Et₂O was added 0.1 mL of HCl.Et₂O (1 M). Stirring was continued for another 20 min at ambient temperature. The title compounds A24, A25 and A27 were obtained after the removal of solvent.

Preparation of B1-B12:

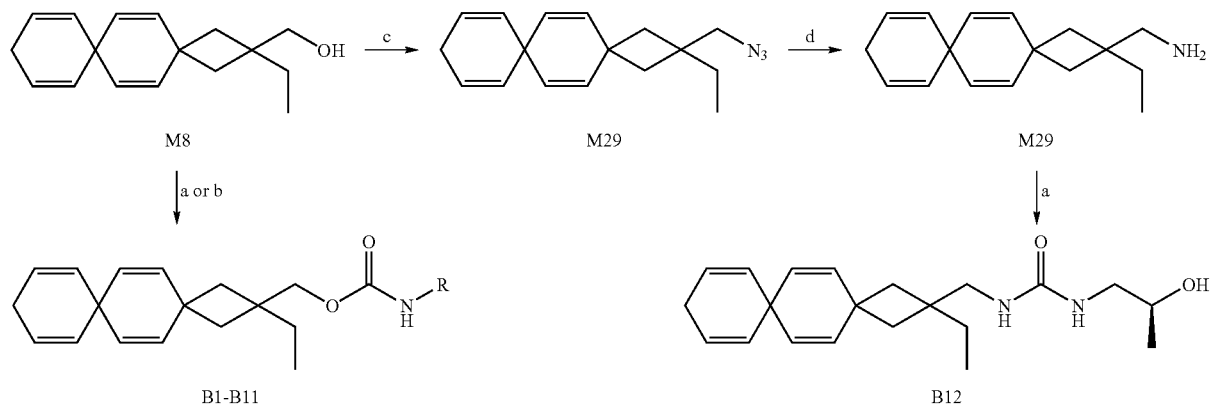

a. CO(imidazole)₂, amines, THF, 70-90%;
b. diphosgene, Et₃N, THF, amines, 85-90%;
c. Zn(N₃)₂•2Py, DIAD, PPh₃ toluene, 0° C.-r.t., 85%;
d. H₄LiAl, Et₂O, 84%;

Compound M26:

To a solution of M25 (1 mmol) in 5 mL anhydrous Et₂O was added 1.5 mL of 1M H₄AlLi in Et₂O at 0° C. Stirring was continued for another 6 h at ambient temperature. The reaction was quenched by 0.06 mL water, 0.06 mmol 15% NaOH and 0.18 mmol water, respectively. The heterogeneous mixture was filtered through a pad of Celite, concentrated in vacuo to give pure M26 (0.95 mmol, 95% yield) as oil.

Compound M27:

ZnN₆.2Py (0.76 mmol) was suspended in a solution of the M26 (0.95 mmol) and PPh₃ (1.9 mmol) in 5 mL of anhydrous toluene. To this stirred mixture at r.t. diisopropyl azodicarboxylate (1.9 mmol) was added dropwise. Stirring was continued until complete consumption (TLC monitoring) of M26 was observed. The heterogeneous mixture was filtered over a Compound B1-B8 and B12

Method A: To a suspension of CO(imidazole)₂ (1.5 mmol) in 3 mL of anhydrous THF was added a solution of M8 (1 mmol) in 1 mL THF at 0° C. Stirring was continued for another 2 h at ambient temperature. Then, the reaction mixture was cooled to 0° C. again, and the respective amine (2 mmol) was added and stirred for overnight. THF was removed in vacuo, and the residue was diluted with Et₂O. The heterogeneous mixture was filtered with a pad of Celite, and filtrate was washed with 2N HCl, saturated NaHCO₃ and brine, respectively, dried over Na₂SO₄. The solvent was removed in vacuo, and residue was chromatographed on silica gel to afford pure B1-B8 (0.6-0.9 mmol, 60-90% yield) as oil.

Compound B9-B11:

Method B: To a suspension of M8 (1 mmol) and activated carbon (0.1 mmol) in 3 mL of anhydrous THF was added diphosgene (0.75 mmol) at 0° C. Stirring was continued for another 2 h at 0° C. Then, a solution of respective amine (2 mmol) Et$_3$N (6 mmol) in 1 mL of THF was added to above reaction mixture and stirring was continued for overnight. It was diluted with Et$_2$O, and heterogeneous mixture was filtered with a pad of Celite. The filtrate was washed with water and brine, dried over Na$_2$SO$_4$ and concentrated in vacuo. The residue was chromatographed to give pure B9-B11 (0.82-0.90 mmol, 82-90% yield) as oil.

Compound M29:

M29 was made by following the procedure of synthesis of M27.

Compound M30:

M30 was synthesized by following the procedure of synthesis of M28.

Preparation of B13-B15:

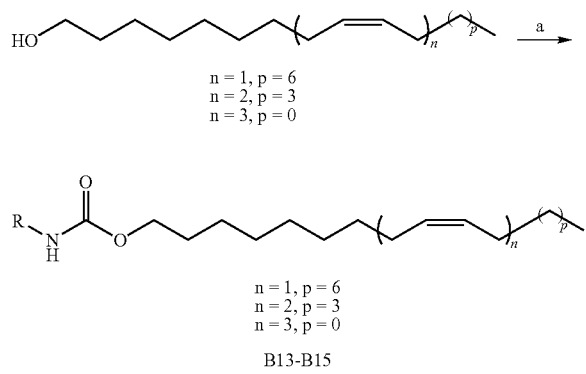

B13-B15 a. CO(imidazole)$_2$, amines, THF, 75-87%.

Compound B13-B15:

Preparation of B13-B15 can be fulfilled from corresponding commercially available alcohols following the procedure of preparation of B1-B8.

Preparation of B16:

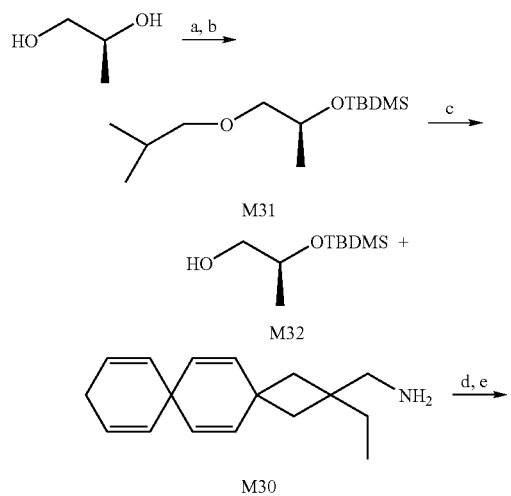

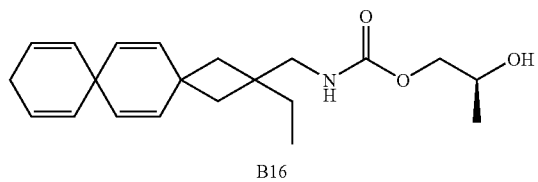

B16 a. 2-methyl-1-butene, BF$_3$•OEt$_2$, CH$_2$Cl$_2$, r.t. 80%
b. TBDMSCl, imidazole, THF, 85%;
c; TBDMSOTf, CH$_2$Cl$_2$, 60%;
d. CO(imidazole)$_2$, amines, THF, 83%
e. TBAF, THF, 80%.

Compound M31:

To a solution of (S)-1,2-propandiol (5 mmol) in 5 mL of anhydrous CH$_2$Cl$_2$ were added 2-methyl-1-butene (5.5 mmol) and BF$_3$ etherate (0.5 mmol) at room temperature. The stirring was continued for another 24 h. The solvent was removed by vacuum, and the residue was purified by chromatograph on silica gel to afford intermediate (4 mmol, 80% yield) as oil. Then, to a suspension of this intermediate and imidazole (6 mmol) in 6 mL of anhydrous THF was added 4.8 mL of TBDMSCl (1M in THF) at 0° C. The solvent was removed by vacuum, and the residue was re-dissolved in Et$_2$O. The heterogeneous mixture was filtered over a pad of Celite. The filtrate was washed with 1N HCl, water and brine, dried over Na$_2$SO$_4$ and concentrated in vacuo. The residue was chromatographed to give pure M31 (0.34 mmol, 85% yield) as oil.

Compound M32:

To a solution of M31 (3 mmol) in 3 mL of anhydrous CH$_2$Cl$_2$ was added TBDMSOTf (0.3 mmol) at room temperature, and the resulting solution was stirred for 24 hours. Saturated NaHCO$_3$ was then added and the solution extracted with AcOEt. Combined organic layers were dried over Na$_2$SO$_4$ and concentrated in vacuo. The crude product was purified by chromatograph on silica gel to afford M32 (1.8 mmol, 60% yield) as oil.

Compound B16:

The B16 can be made in two steps. The first one is coupling, which can be fulfilled by following the similar procures of preparation of B1-B8 in 83% yield. The second step is deprotection by TBAF. To a solution of coupling product (1 mmol) in 2 mL of THF was added 1.2 mL of TBAF (1M in THF) at room temperature. The stirring was continued for another 1.5 h. Then, the THF was removed in vacuum, and the resulting mixture was dissolved in Et$_2$O. The resulting solution was washed by water and brine, dried over Na$_2$SO$_4$ and concentrated in vacuum. The crude product was purified by chromatograph on silica gel to afford B16 (0.8 mmol, 80% yield) as oil.

Preparation of Compound A28-30

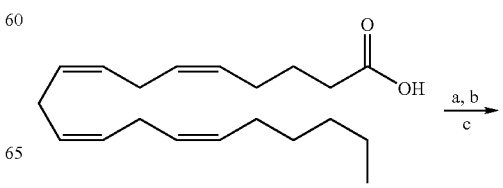

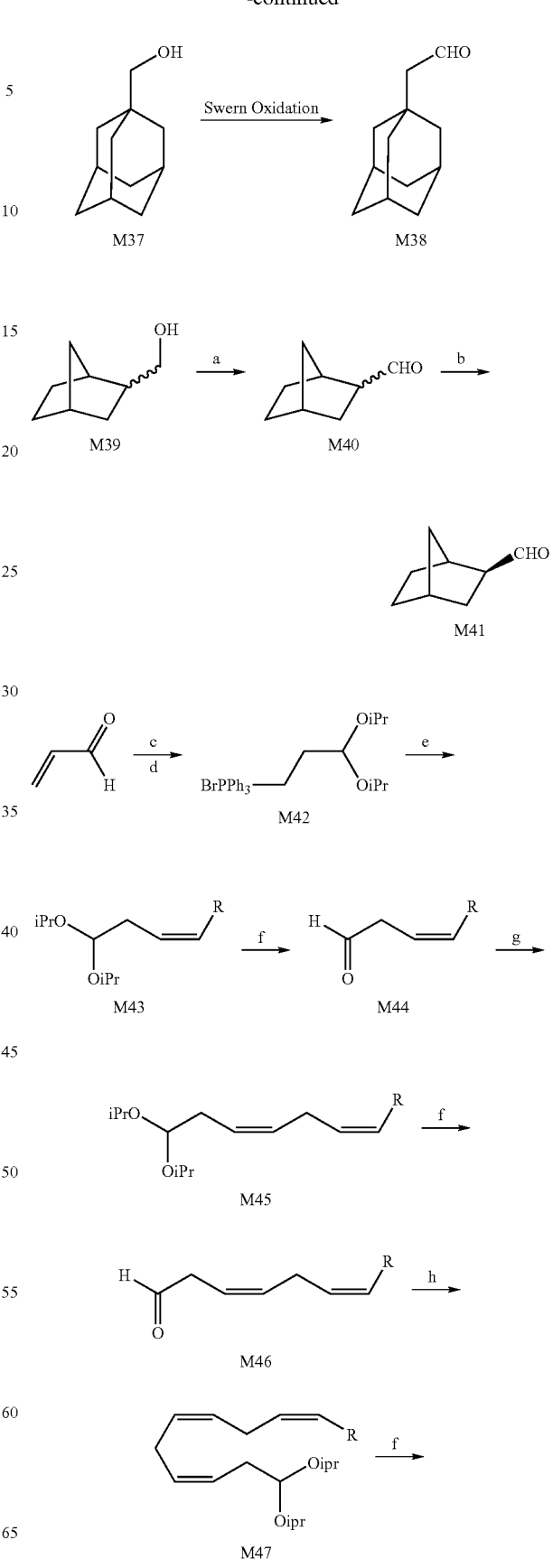
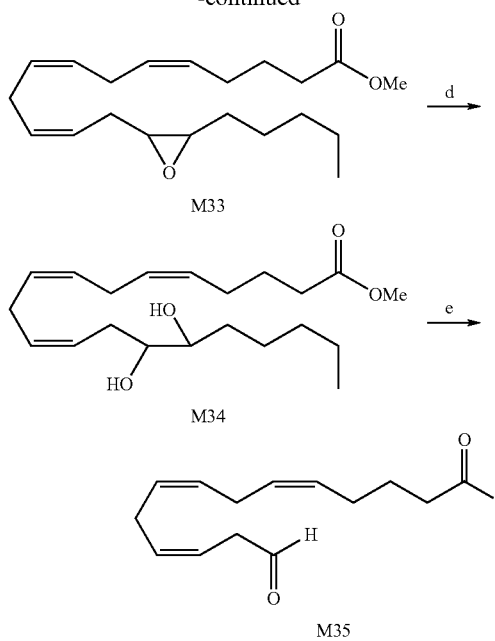
a) CO (imidazole)$_2$; b) H$_2$O$_2$; c) CO(imidazole)$_2$; MeOH(30-55% overall yield); HClO$_4$(aq)/ether (62-70%); e) Pb(OAc)$_4$ (68-72%)
a) PPh$_3$, ZnI$_2$, DEAD (65%); b) PPh$_3$, heating (80%); c) LiHMDS +M31; d) D-alaninol, MeOH, CuCN (50%).

31
-continued

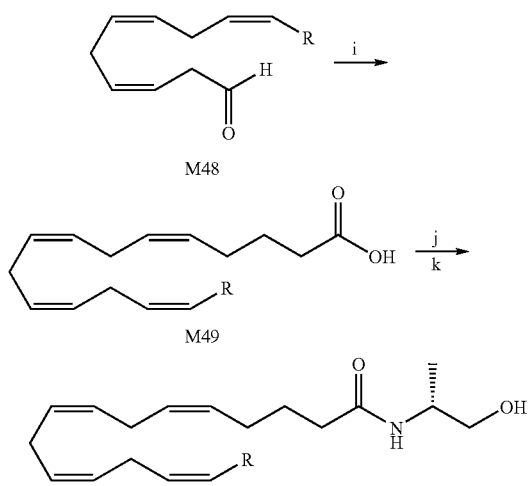

32
-continued

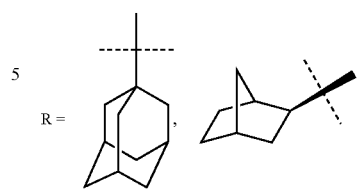

a) PDC/Celite (72%); b) K₂CO₃/MeOH (48%); c) HBr, PPh₃; d) triisopropyl orthoformate (53% over 2 steps); e) NaHMDS + M34 or M37; f) TsOH, THF, heating; g) NaHMDS + M38, (71% 2 steps); h) NaHMDS, + M38; i) NaHMDS (2 eq), 5-triphenylphosphonium bromide pentanoic acid (50% over 2 steps); j) oxalyl chloride, DMF, bz; k) D-ananinol, MeOH, CuCN (50% over 2 steps).

Those skilled in the art will recognize, or be able to ascertain with no more than routine experimentation, many equivalents to the specific embodiments of the invention disclosed herein. Such equivalents are intended to be encompassed by the scope of the invention.

TABLE 1

Exemplary Compounds of Formula I

| Analogues | | Ki CB1 (nM) (o/w PMSFQ) | CB2 (nM) | $IC_{50}$ AT inhibition (μM) | FAAH % Inhibition | Mag-Lipase % Inhibition | COX-2 % Inhibition |
|---|---|---|---|---|---|---|---|
| A1 | | 94.6/153.0 | 176.5 | ND | 23 | 20.5 | 78.4 |
| A2 | | 729.4/128.8 | 171.0 | ND | 32 | 37.5 | NA |
| A3 | | 182.9/58.6 | 83.3 | 9.1 | 34 | 16.7 | 77.4 |
| A4 | | 1180/84.3 | 1228 | ND | 58 | 9.2 | NA |

TABLE 1-continued

Exemplary Compounds of Formula I

| Analogues | | Ki CB1 (nM) (o/w PMSFQ) | CB2 (nM) | IC$_{50}$ AT inhibition (μM) | FAAH % Inhibition | Mag-Lipase % Inhibition | COX-2 % Inhibition |
|---|---|---|---|---|---|---|---|
| A5 | | 26.7/0.9 | 57.6 | 2.9 | 7 | ND | ND |
| A6 | | 194.7/113.8 | 426 | ND | 11 | 20.7 | NA |
| A7 | | 164.8/80.5 | 302.4 | ND | 46 | 13.7 | 42.4 |
| A8 | | 1296/105.9 | 513.3 | 2.3 | 49 | NA | NA |
| A9 | | 112.1/31.9 | 72.4 | ND | 58 | NA | NA |
| A10 | | 95.2/7.7 | 52.7 | ND | 84 | ND | ND |
| A11 | | 91.7/34.2 | 70.9 | ND | 90 | ND | ND |

TABLE 1-continued

Exemplary Compounds of Formula I

| Analogues | | Ki CB1 (nM) (o/w PMSFQ) | CB2 (nM) | IC$_{50}$ AT inhibition (μM) | FAAH % Inhibition | Mag-Lipase % Inhibition | COX-2 % Inhibition |
|---|---|---|---|---|---|---|---|
| A12 | arachidonoyl-N-(4-hydroxy-3-methoxybenzyl) amide with NCS chain | 192.7/135.9 | 553.1 | ND | 39 | NA | 46.2 |
| A13 | arachidonoyl-N-(4-hydroxyphenyl) amide with N$_3$ chain | 3833/531.5 | 334.8 | 0.7 | 33 | ND | ND |
| A14 | arachidonoyl-N-thiazoline amide with N$_3$ chain | 428.1/144.1 | 242.9 | 1.2 | 48 | ND | ND |
| A15 | arachidonoyl-N-(4-hydroxy-3-methoxybenzyl) amide with N$_3$ chain | 48.8/13.2 | 74.7 | ND | 38 | ND | ND |
| A16 | arachidonoyl-N-cyclopropyl amide with SCN chain | 83.7/1.3 | 48.5 | 1.9 | 43 | 5.2 | ND |
| A17 | arachidonoyl-N-cyclopropyl amide with HO chain | 208.9/3.9 | 38.7 | 35.3 | 61 | ND | ND |

TABLE 1-continued

Exemplary Compounds of Formula I

| Analogues | | Ki CB1 (nM) (o/w PMSFQ) | CB2 (nM) | IC$_{50}$ AT inhibition (μM) | FAAH % Inhibition | Mag-Lipase % Inhibition | COX-2 % Inhibition |
|---|---|---|---|---|---|---|---|
| A18 | (structure with cyclopropyl amide and Br) | 25.1/0.16 | 12.3 | 6.7 | 72 | 22.5 | ND |
| A19 | (structure with cyclopropyl amide and NC) | 32.9/0.04 | 5.7 | 23.5 | 57 | NA | ND |
| A20 | (structure with cyclopropyl amide and Cl) | 57.9/0.17 | 28.3 | 4.1 | 67 | NA | ND |
| A21 | (structure with cyclopropyl amide and N-methyl-butyl) | 76.5/66.3 | 237.6 | ND | ND | ND | ND |
| A22 | (structure with OMe amide and N-methyl-butyl) | 28.0/3.9 | 224.0 | ND | ND | ND | ND |
| A23 | (structure with acetamide and N-methyl-butyl) | 812.7/626.5 | 1764 | ND | ND | ND | ND |

TABLE 1-continued

Exemplary Compounds of Formula I

| Analogues | | Ki CB1 (nM) (o/w PMSFQ) | CB2 (nM) | IC$_{50}$ AT inhibition (μM) | FAAH % Inhibition | Mag-Lipase % Inhibition | COX-2 % Inhibition |
|---|---|---|---|---|---|---|---|
| A24 | [structure] | 351/51.8 | 434.8 | ND | ND | ND | ND |
| A25 | [structure] | 1503/1032 | 3652 | ND | ND | ND | ND |
| A26 | [structure] | 4717/2151 | 2914 | 5.4 | ND | 9.8 | NA |
| A27 | [structure] | 2217/1624 | 2559 | 7.1 | ND | 4.2 | NA |
| A28 | [structure] | NA | 3459 | ND | ND | ND | ND |
| A29 | [structure] | NA | 5667 | ND | ND | ND | ND |

TABLE 1-continued

Exemplary Compounds of Formula I

| Analogues | | Ki CB1 (nM) (o/w PMSFQ) | CB2 (nM) | IC$_{50}$ AT inhibition (µM) | FAAH % Inhibition | Mag-Lipase % Inhibition | COX-2 % Inhibition |
|---|---|---|---|---|---|---|---|
| A30 | [structure] | NA | NA | ND | ND | ND | ND |

NA: no activity;
ND: not determined.
AT: anandamide transporter
o/w PMSF: data obtained without or with phenyl methyl sulfonyl flouride

TABLE 2

Exemplary compounds of Formula II

| Analogues | | Ki CB1 (nM) (o/w PMSF) | CB2 (nM) | IC$_{50}$ (AT inhib.) (µM) | (FAAH) % Inhibition | Mag-Lipase % Inhibition | COX-2 % Inhibition |
|---|---|---|---|---|---|---|---|
| B1 | [structure] | 1326/1440 | 5067 | 7.1 | 14.7 | | |
| B2 | [structure] | 1100/996.5 | 2147 | 6.4 | 14.3 | | |
| B3 | [structure] | 526/396 | 597 | 1.5 | 10 | 14.3 | |
| B4 | [structure] | 338/320 | 254 | 0.4 | 7 | | |
| B5 | [structure] | 510.3/343.4 | 543.2 | 21.9 | 4.5 | | |
| B6 | [structure] | 181.2/75.1 | 983.3 | 15.5 | NA | | |
| B7 | [structure] | 1412/994.6 | 5309 | 15.5 | NA | | |

TABLE 2-continued

Exemplary compounds of Formula II

| Analogues | | Ki CB1 (nM) (o/w PMSF) | CB2 (nM) | IC$_{50}$ (AT inhib.) (μM) | (FAAH) % Inhibition | Mag-Lipase % Inhibition | COX-2 % Inhibition |
|---|---|---|---|---|---|---|---|
| B8 | AA-O-C(O)-NH-cyclohexyl | 3956/1474 | 781.1 | 33.0 | NA | | |
| B9 | AA-O-C(O)-NH-C$_6$H$_4$-OH | 5386/3297 | 532.7 | 6.6 | 27.3 | | |
| B10 | AA-O-C(O)-NH-thiazoline | No data | No data | 8.6 | ND | 34.0 | NA |
| B11 | AA-O-C(O)-NH-pyridyl | 302.1/96.4 | 185.4 | 16.1 | ND | 16.8 | |
| B12 | AA-NH-C(O)-NH-CH$_2$-CH(CH$_3$)-OH | 380/125.5 | 241.6 | 1.78 | 17.2 | 11.1 | |
| B13 | OLE-O-C(O)-NH-CH$_2$-CH(OH)-CH$_3$ | 4747/2237 | 2600 | 5.92 | NA | 13.1 | |
| B14 | LIE-O-C(O)-NH-CH$_2$-CH(OH)-CH$_3$ | 1346/404.6 | 2252 | 7.21 | 1.20 | 25.8 | |
| B15 | LIN-O-C(O)-NH-CH$_2$-CH(OH)-CH$_3$ | 622/481 | 421.5 | 4.50 | 6.96 | 24.6 | |
| B16 | AA-NH-C(O)-O-CH$_2$-CH(OH)-CH$_3$ | 1204/686.3 | 289.4 | 3.29 | ND | | |

AA:

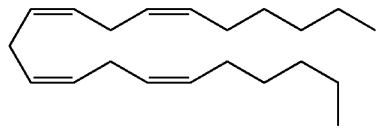

OLE:

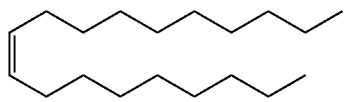

TABLE 2-continued

Exemplary compounds of Formula II

| Analogues | Ki CB1 (nM) (o/w PMSF) | CB2 (nM) | IC$_{50}$ (AT inhib.) (µM) | (FAAH) % Inhibition | Mag-Lipase % Inhibition | COX-2 % Inhibition |
|---|---|---|---|---|---|---|
| LIE: | | | | | | |
| LIN: | | | | | | |

NA: no activity
ND: not determined
AT: anandamide transporter
o/w PMSF: data obtained without or with phenyl methyl sulfonyl fluoride

The invention claimed is:

1. A compound of Formula I or Formula II, including any possible isomer, stereoisomer and enantiomer and, physiologically acceptable salts thereof, wherein Formula I is:

R$^a$-FA-M-R$_b$, and

FA is a long chain hydrocarbon comprising 2 to 22 carbons and 0 to 6 double bonds, the double bonds can be conjugated or unconjugated, the FA long chain hydrocarbon is optionally substituted in any possible position with one or more lower-alkyl, di-lower-alkyl, cycloalkyl or heterocycloalkyl groups, the FA long chain hydrocarbon is optionally interrupted with, or includes, one or more of methylene, (CH$_3$)$_2$C, O, NH, N-alkyl, cyclic group, heterocyclic group and aryl;

M is X—Y—Z,
  X is optionally present and if present is selected from NH, N-lower alkyl, O and CH—NHR where R is selected from H, Boc or another group similar in size to Boc,
  Y is selected from C=O, C=S, C=NH, S=O, SO$_2$, SO$_3$, O=C—C=O and CHNH$_2$,
  Z is optionally present and if present is selected from O, NH, N-lower alkyl, and NQ$_1$Q$_2$ wherein Q$_1$ and Q$_2$ each independently comprise H or alkyl, or Q$_1$ and Q$_2$ together comprise a phthalimido group or a part of a heterocyclic ring having 3 to about 7 ring members and optionally including one additional ring heteroatom selected from O, N, S;

R$_a$ is selected from E$_1$-X$_1$-E$_2$-T$_1$ and E$_1$-E$_2$-T$_1$,
  E$_1$ and E$_2$ are each independently selected from alkyl, alkenyl and alkynyl having 0 to 10 carbons and optionally substituted with lower alkyl or di-lower-alkyl,
  X$_1$ is selected from NH, N-lower-alkyl and O,
  T$_1$ is selected from aryl, carbocyclic ring, bicyclic ring, tricyclic ring, heterocyclic ring, heterobicyclic ring, heterotricyclic ring, heteroaromatic ring, OH, SH, halogen, C(halogen)$_3$, CH(halogen)$_2$, O-alkyl, N$_3$, CN, NCS, NH$_2$, alkylamino, dialkylamino and a substituent group;

R$_b$ is selected from —(CH$_2$)$_m$—(C(CH$_3$)$_2$)$_p$—(CH$_2$)$_n$-T$_2$-T$_3$, and —(CH$_2$)$_m$—(CH(CH$_3$))$_q$—(CH$_2$)$_n$-T$_2$-T$_3$, where m and n are each an integer independently selected from 0 to 6; p and q are each an integer independently selected from 0 to 1, T$_2$ is optionally present and if present is selected from aryl, carbocyclic ring, bicyclic ring, tricyclic ring, heterocyclic ring, heterobicyclic ring, heterotricyclic ring heteroaromatic ring, 1- or 2-glycerol, 1- or 2-cyclic glycerol, alkyl, alkenyl, and alkynyl, T$_3$ is selected from SH, halogen, C(halogen)$_3$, CH(halogen)$_2$, O-alkyl, N$_3$, CN, NCS, NH$_2$, alkylamino, dialkylamino and a substituent group; or Formula II is:

R-M-R', and

R is a fatty acid tail remnant having 16 to 24 carbons or an alkyl-substituted fatty acid tail remnant having 16 to 24 carbons;

M is X—Y—Z, and
  X is optionally present and if present is selected from NH, N-lower alkyl, O and CH—NHR where R comprises H, Boc or another group similar in size to Boc,
  Y is selected from C=O, C=S, C=NH, S=O, SO$_2$, SO$_3$, O=C—C=O and CHNH$_2$; and
  Z is optionally present and if present is selected from O, NH, N-lower alkyl, and NQ$_1$Q$_2$ wherein Q$_1$ and Q$_2$ each independently comprise H or alkyl, or Q$_1$ and Q$_2$ together comprise a phthalimido group, or a part of a heterocyclic ring having 3 to about 7 ring members and optionally including one additional ring heteroatom selected from O, N, S;

R' is selected from —(CH$_2$)$_m$—(C(CH$_3$)$_2$)$_p$—(CH$_2$)$_n$-T$_2$-T$_3$, and —(CH$_2$)$_m$—(CH(CH$_3$))$_q$—(CH$_2$)$_n$-T$_2$-T$_3$, where m and n are each an integer independently selected from 0 to 6; and where p and q are each an integer independently selected from 0 or 1, T$_2$ is optionally present and if present is selected from aryl, carbocyclic ring, bicyclic ring, tricyclic ring, heterocyclic ring, heterobicyclic ring, heterotricyclic ring, heteroaromatic ring, 1- or 2-glycerol, 1- or 2-cyclic glycerol, alkyl, alkenyl, and alkynyl;

T$_3$ is selected from SH, halogen, C(halogen)$_3$, CH(halogen)$_2$, O-alkyl, N$_3$, CN, NCS, NH$_2$, alkylamino, dialkylamino and a substituent group;

with the following provisos with respect to the compounds of Formula II:

when M is O—C(O)—NH and R is the tail remnant of arachidonyl acid, R' excludes ethyl, iso-propyl and propyl;

when M is NH—C(O)—NH and R is the tail remnant of arachidonyl acid, R' excludes methyl, iso-propyl, propyl, iso-butyl, $CH_2CH_2F$, $CH_2CH_2OH$, and CH2CH2OCH3;

when M is NH—C(O)—O and R is the tail remnant of arachidonyl acid, R' excludes ethyl, iso-propyl and $CH_2CH_2F$; and when M is NH—C(S)—NH and R is the tail remnant of arachidonyl acid, R' excludes 4 methyl-2-methoxy-phenol, and 4-methyl-2-chloro-phenol.

2. The compound of claim 1 wherein:

FA is a long chain hydrocarbon comprising 12 to 22 carbons and 4 methylene-interrupted cis double bonds; and the X1 of $R^a$ is selected from NH and N-lower alkyl; or FA is a long chain hydrocarbon comprising 12 to 22 carbons and 4 methylene-interrupted cis double bonds; and $R^a$ is $E_1$-$E_2$-$T_1$ wherein $T_1$ is selected from aryl, heteroaromatic ring, carbocyclic ring, bicyclic ring, tricyclic ring, heterocyclic ring; or FA is a long chain hydrocarbon comprising 12 to 22 carbons and 4 methylene-interrupted cis double bonds; and $R^a$ is $E_1$-$E_2$-$T_1$ wherein $T_1$ is selected from OH, SH, halogen, $C(halogen)_3$, $CH(halogen)_2$, O-alkyl, $N_3$, CN, NCS, $NH_2$, alkylamino and dialkylamino.

3. A pharmaceutical preparation containing a therapeutically effective amount of a compound of claim 1, or a physiologically acceptable salt thereof.

4. A method of stimulating a cannabinoid receptor in an individual or animal comprising administering to the individual or animal a pharmaceutical preparation comprising a therapeutically effective amount of a compound of Formula I or Formula II, including any possible isomer, stereoisomer and enantiomer and, physiologically acceptable salts thereof, wherein Formula I is:

$R_a$-FA-M-$R_b$, and

FA is a long chain hydrocarbon comprising 2 to 22 carbons and 0 to 6 double bonds, the double bonds can be conjugated or unconjugated, the FA long chain hydrocarbon is optionally substituted in any possible position with one or more lower-alkyl, di-lower-alkyl, cycloalkyl or heterocycloalkyl groups, the FA long chain hydrocarbon is optionally interrupted with, or includes, one or more of methylene, $(CH_3)_2C$, O, NH, N-alkyl, cyclic group, heterocyclic group and aryl;

M is X—Y—Z,

X is optionally present and if present is selected from NH, N-lower alkyl, O and CH—NHR where R is selected from H, Boc or another group similar in size to Boc, Y is selected from C=O, C=S, C=NH, S=O, $SO_2SO_3$, O=C—C=O and $CHNH_2$, Z is optionally present and if present is selected from O, NH, N-lower alkyl, and $NQ_1Q_2$, wherein $Q_1$ and $Q_2$ each independently comprise H or alkyl, or $Q_1$ and $Q_2$ together comprise a phthalimido group or a part of a heterocyclic ring having 3 to about 7 ring members and optionally including one additional ring heteroatom selected from O, N, S;

$R_a$ is selected from $E_1$-$X_1$-$E_2$-$T_1$ and $E_1$-$E_2$-$T_1$, $E_1$ and $E_2$, are each independently selected from alkyl, alkenyl and alkynyl having 0 to 10 carbons and optionally substituted with lower alkyl or di-lower-alkyl, $X_1$ is selected from NH, N-lower-alkyl and O, $T_1$ is selected from aryl, carbocyclic ring, bicyclic ring, tricyclic ring, heterocyclic ring, heterobicyclic ring, heterotricyclic ring, heteroaromatic ring, OH, SH, halogen, $C(halogen)_3$, $CH(halogen)_2$, O-alkyl, $N_3$, CN, NCS, $NH_2$, alkylamino, dialkylamino and a substituent group;

$R^b$ is selected from —$(CH_2)_m$—$(C(CH_3)_2)_p$—$(CH_2)_n$-$T_2$-$T_3$, and —$(CH_2)_m$—$(CH(CH_3))_q$—$(CH_2)_n$-$T_2$-$T_3$, where m and n are each an integer independently selected from 0 to 6; p an q are each an integer independently selected from 0 to 1, $T_2$ is optionally present and if present is selected from aryl, carbocyclic ring, bicyclic ring, tricyclic ring, heterocyclic ring, heterobicyclic ring, heterotricyclic ring heteroaromatic ring, 1- or 2-glycerol, 1- or 2-cyclic glycerol, alkyl, alkenyl, and alkynyl, $T_3$ selected from SH, halogen, $C(halogen)_3$, $CH(halogen)_2$, O—alkyl, $N_3$, CN, NCS, $NH_2$, alkylamino, dialkylamino and a substituent group; or Formula II is:

R-M-R', and

R is a fatty acid tail remnant having 16 to 24 carbons or an alkyl-substituted fatty acid tail remnant having 16 to 24 carbons;

M is X—Y—Z, and

X is optionally present and if present is selected from NH, N-lower alkyl, O and CH—NHR where R comprises H, Boc or another group similar in size to Boc, Y is selected from C=O, C=S, C=NH, S=O, $SO_2$, $SO_3$, O=C—C=O and $CHNH_2$; and Z is optionally present and if present is selected from O, NH, N-lower alkyl, and $NQ_1Q_2$ wherein $Q_1$ and $Q_2$ each independently comprise H or alkyl, or $Q_1$ and $Q_2$ together comprise a phthalimido group, or a part of a heterocyclic ring having 3 to about 7 ring members and optionally including one additional ring heteroatom selected from O, N, S;

R' is selected from —$(CH_2)_m$—$(C(CH_3)_2)_p$—$(CH_2)_n$-$T_2$-$T_3$, and —$(CH_2)_m$—$(CH(CH_3))_q$—$(CH_2)_n$-$T_2$-$T_3$, where m and n are each an integer independently selected from 0 to 6; and where p and q are each an integer independently selected from 0 or 1.

$T_2$ is optionally present and if present is selected from aryl, carbocyclic ring, bicyclic ring, tricyclic ring, heterocyclic ring, heterobicyclic ring, heterotricyclic ring, heteroaromatic ring, 1- or 2-glycerol, 1- or 2-cyclic glycerol, alkyl, alkenyl, and alkynyl;

$T_3$ is selected from SH, halogen, $C(halogen)_3$, $CH(halogen)_2$, O-alkyl, $N_3$, CN, NCS, $NH_2$, alkylamino, dialkylamino and a substituent group;

with the following provisos with respect to the compounds of Formula II:

when M is O—C(O)—NH and R is the tail remnant of arachidonyl acid, R' excludes ethyl, iso-propyl and propyl;

when M is NH—C(O)—NH and R is the tail remnant of arachidonyl acid, R' excludes methyl, iso-propyl, propyl, iso-butyl, $CH_2CH_2F$, $CH_2CH_2OH$, and CH2CH2OCH3;

when M is NH—C(O)—O and R is the tail remnant of arachidonyl acid, R' excludes ethyl, iso-propyl and $CH_2CH_2F$; and when M is NH—C(S)—NH and R is the tail remnant of arachidonyl acid, R' excludes 4 methyl-2-methoxy-phenol, and 4-methyl-2-chloro-phenol.

5. A method of providing a physiological effect in an individual or animal comprising administering to the individual or animal a pharmaceutical preparation comprising a therapeutically effective amount of a compound of claim 1 or a physiologically acceptable salt thereof.

6. The method of claim 4, wherein one of a CB1 or CB2 cannabinoid receptor in the individual or animal is preferentially stimulated without stimulating the other of the CB1 or CB2 cannabinoid receptor to the same extent.

7. A method of inhibiting transport of anandamide in an individual or animal comprising administering to the individual or animal a pharmaceutical preparation comprising a therapeutically effective amount of a compound of Formula I or Formula II, including any possible isomer, stereoisomer and enantiomer and, physiologically acceptable salts thereof, wherein Formula I is:

$R_a$FA-M-$R_b$, and

FA is a long chain hydrocarbon comprising 2 to 22 carbons and 0 to 6 double bonds, the double bonds can be conjugated or unconjugated, the FA long chain hydrocarbon is optionally substituted in any possible position with one or more lower-alkyl, di-lower-alkyl, cycloalkyl or heterocycloalkyl groups, the FA long chain hydrocarbon is optionally interrupted with, or includes, one or more of methylene, $(CH_3)_2C$, O, NH, N-alkyl, cyclic group, heterocyclic group and aryl;

M is X—Y—Z,

X is optionally present and if present is selected from NH, N-lower alkyl, O and CH—NHR where R is selected from H, Boc or another group similar in size to Boc, Y is selected from C=O, C=S, C=NH, S=O, $SO_2$, $SO_3$, O=C—C=O and $CHNH_2$, Z is optionally present and if present is selected from O, NH, N-lower alkyl, and $NQ_1Q_2$ wherein $Q_1$ and $Q_2$ each independently comprise H or alkyl, or $Q_1$ and $Q_2$ together comprise a phthalimido group or a part of a heterocyclic ring having 3 to about 7 ring members and optionally including one additional ring heteroatom selected from O, N, S;

$R_a$ is selected from $E_1$-$X_1$-$E_2$-$T_1$ and $E_1$-$E_2$-$T_1$, $E_1$ and $E_2$ are each independently selected from alkyl, alkenyl and alkynyl having 0 to 10 carbons and optionally substituted with lower alkyl or di-lower-alkyl, $X_1$ is selected from NH, N-lower-alkyl and O, $T_1$ is selected from aryl, carbocyclic ring, bicyclic ring, tricyclic ring, heterocyclic ring, heterobicyclic ring, heterotricyclic ring, heteroaromatic ring, OH, SH halogen, C(halogen)$_3$, CH(halogen)$_2$, O-alkyl, $N_3$, CN, NCS, $NH_2$, alkylamino, dialkylamino and a substituent group;

$R_b$ is selected from —$(CH_2)_m$—$(C(CH_3)_2)_p$—$(CH_2)_n$-$T_2$-$T_3$, and —$(CH_2)_m$—$(CH(CH_3))_q$—$(CH_2)_n$-$T_2$-$T_3$, where m and n are each an integer independently selected from 0 to 6; p and q are each an integer independently selected from 0 to 1, $T_2$ is optionally present and if present is selected from aryl, carbocyclic ring, bicyclic ring, tricyclic ring, heterocyclic ring, heterobicyclic ring, heterotricyclic ring heteroaromatic ring, 1- or 2-glycerol, 1- or 2-cyclic glycerol, alkyl, alkenyl, and alkynyl, $T_3$ is selected from SH, halogen, C(halogen)$_3$, CH(halogen)$_2$, O-alkyl, $N_3$, CN, NCS, $NH_2$, alkylamino, dialkylamino and a substituent group; or Formula II is:

R-M-R', and

R is a fatty acid tail remnant having 16 to 24 carbons or an alkyl-substituted fatty acid tail remnant having 16 to 24 carbons;

M is X—Y—Z, and

X is optionally present and if present is selected from NH, N-lower alkyl, O and CH—NHR where R comprises H, Boc or another group similar in size to Boc, Y is selected from C=O, C=S, C=NH, S=O, SO—, $SO$—, O=C—C=O and $CHNH_2$; and Z is optionally present and if resent is selected from O, NH, N-lower alkyl and $NQ_1Q_2$ wherein $Q_1$ and $Q_2$ each independently comprise H or alkyl, or $Q_1$ and $Q_2$ together comprise a phthalimido group or a part of a heterocyclic ring having 3 to about 7 ring members and optionally including one additional ring heteroatom selected from O, N, S;

R' is selected from —$(CH_2)_m$—$(C(CH_3)_2)_p$—$(CH_2)_n$-$T_2$-$T_3$, and —$(CH_2)_m$—$(CH(CH_3))_q$—$(CH_2)_n$-$T_2$-$T_3$, where m and n are each an integer independently selected from 0 to 6 and where p and q are each an integer independently selected from 0 or 1, $T_2$ is optionally present and if present is selected from aryl, carbocyclic ring, bicyclic ring, tricyclic ring, heterocyclic ring, heterobicyclic ring, heterotricyclic ring, heteroaromatic ring, 1- or 2-qlycerol, 1- or 2-cyclic qlycerol, alkyl, alkenyl, and alkynyl;

$T_3$ is selected from SH, halogen, C(halogen)$_3$ CH(halogen)$_2$, O-alkyl, $N_3$, CN, NCS, $NH_2$, alkylamino, dialkylamino and a substituent group;

with the following provisos with respect to the compounds of Formula II:

when M is O—C(O)—NH and R is the tail remnant of arachidonyl acid, R' excludes ethyl, iso-propyl and propyl;

when M is NH—C(O)—NH and R is the tail remnant of arachidonyl acid, R' excludes methyl, iso-propyl, propyl, iso-butyl, $CH_2CH_2CH_2OH$, and CH2CH2OCH3;

when M is NH—C(O)—O and R is the tail remnant of arachidonyl acid, R' excludes ethyl, iso-propyl and $CH_2CH_2F$; and when M is NH—C(S)—NH and R is the tail remnant of arachidonyl acid, R' excludes 4 methyl-2-methoxy-phenol, and 4-methyl-2-chloro-phenol.

8. A method of inhibiting enzymes that moderate biodisposal of cannabinoids in an individual or animal comprising administering to the individual or animal a therapeutically effective amount of a compound of claim 1 or a physiologically acceptable salt thereof.

9. The compound of claim 1 selected from Formula II.

10. The preparation of claim 3 wherein the compound is in isolated and substantially purified form.

11. The preparation of claim 3 further comprising at least one member selected from a carrier, a vehicle, an adjuvant, a flavoring, a colorant, or a preservative and the compound is in isolated and substantially purified form.

12. The method of claim 4 wherein the compound is selected from Formula II.

13. The method of claim 4 wherein the compound is selected from Formula I; and

FA is a long chain hydrocarbon comprising 12 to 22 carbons and 4 methylene-interrupted cis double bonds; and the X1 of $R_a$ is selected from NH and N-lower alkyl; or FA is a long chain hydrocarbon comprising 12 to 22 carbons and 4 methylene-interrupted cis double bonds; and $R^a$ is $E_1$-$E_2$-$T_1$ wherein $T_1$ is selected from aryl, heteroaromatic ring, carbocyclic ring, bicyclic ring, tricyclic ring, heterocyclic ring, heterobicyclic ring and heterotricyclic ring; or FA is a long chain hydrocarbon comprising 12 to 22 carbons and 4 methylene-interrupted cis double bonds; and $R_a$ is $E_1$-$E_2$-$T_1$ wherein $T_1$ is selected from OH, SH, halogen, C(halogen)$_3$, CH(halogen)$_2$, O-alkyl, N$_3$, CN, NCS, NH$_2$, alkylamino and dialkylamino.

14. The method of claim 4 wherein the compound is selected from Formula II.

15. The method of claim 7 wherein the compound is selected from Formula I; and

FA is a long chain hydrocarbon comprising 12 to 22 carbons and 4 methylene-interrupted cis double bonds; and the X1 of $R_a$ is selected from NH and N-lower alkyl; or FA is a long chain hydrocarbon comprising 12 to 22 carbons and 4 methylene-interrupted cis double bonds; and $R^a$ is $E_1$-$E_2$-$T_1$ wherein $T_1$ is selected from aryl, heteroaromatic ring, carbocyclic ring, bicyclic ring, tricyclic ring, heterocyclic ring, heterobicyclic ring and heterotricyclic ring; or FA is a long chain hydrocarbon comprising 12 to 22 carbons and 4 methylene-interrupted cis double bonds; and $R^a$ is $E_1$-$E_2$-$T_1$ wherein $T_1$ is selected from OH, SH, halogen, C(halogen)$_3$, CH(halogen)$_2$, O-alkyl, N$_3$, CN, NCS, NH$_2$, alkylamino and dialkylamino.

16. The method of claim 7 wherein the compound is selected from Formula II.

17. The method of claim 8 wherein the compound is selected from Formula I; and

FA is a long chain hydrocarbon comprising 12 to 22 carbons and 4 methylene-interrupted cis double bonds; and the X1 of $R_a$ is selected from NH and N-lower alkyl; or FA is a long chain hydrocarbon comprising 12 to 22 carbons and 4 methylene-interrupted cis double bonds; and $R^a$ is $E_1$-$E_2$-$T_1$ wherein $T_1$ is selected from aryl, heteroaromatic ring, carbocyclic ring, bicyclic ring, tricyclic ring, heterocyclic ring, heterobicyclic ring and heterotricyclic ring; or FA is a long chain hydrocarbon comprising 12 to 22 carbons and 4 methylene-interrupted cis double bonds; and $R_a$ is $E_1$-$E_2$-$T_1$ wherein $T_1$ is selected from OH, SH, halogen, C(halogen)$_3$, CH(halogen)$_2$, O-alkyl, N$_3$, CN, NCS, NH$_2$, alkylamino and dialkylamino.

18. The method of claim 8 wherein the compound is part of a pharmacological preparation and is in isolated and substantially purified form.

* * * * *

UNITED STATES PATENT AND TRADEMARK OFFICE
CERTIFICATE OF CORRECTION

PATENT NO.         : 8,202,893 B2
APPLICATION NO.    : 11/577156
DATED              : June 19, 2012
INVENTOR(S)        : Makriyannis et al.

It is certified that error appears in the above-identified patent and that said Letters Patent is hereby corrected as shown below:

Column 45, line 28, Claim 1:
delete "$R^a$-FA-M-$R_b$" and insert -- $R_a$-FA-M-$R_b$ --

Column 45, line 58, Claim 1:
delete "0" and insert -- O --

Column 47, line 7, Claim 1:
delete "CH2CH2OCH3" and insert -- $CH_2CH_2OCH_3$ --

Column 47, line 17, Claim 2:
delete "$R^a$" and insert -- $R_a$ --

Column 47, line 22, Claim 2:
after "heterocyclic ring" insert -- , heterobicyclic ring and heterotricyclic ring --

Column 47, line 55, Claim 4:
delete "$SO_2SO_3$" and insert -- $SO_2$, $SO_3$ --

Column 47, line 64, Claim 4:
after "$E_1$ and $E_2$" delete ","

Column 48, line 8, Claim 4:
delete "$R^b$ is selected from —$(CH_2)_m(C(CH_3)_2)_p$—$(CH_2)_n$-$T_2$-$T_3$" and insert -- $R_b$ is selected from —$(CH_2)_m$—$(C(CH_3)_2)_p$—$(CH_2)_n$-$T_2$-$T_3$ --

Column 48, line 11, Claim 4:
delete "p an q" and insert -- p and q --

Signed and Sealed this
Fourth Day of September, 2012

David J. Kappos
*Director of the United States Patent and Trademark Office*

CERTIFICATE OF CORRECTION (continued)
U.S. Pat. No. 8,202,893 B2

Column 48, line 18, Claim 4:
after "$T_3$" insert -- is --

Column 48, line 61, Claim 4:
delete "CH2CH2OCH3" and insert -- $CH_2CH_2OCH_3$ --

Column 49, lines 55-56, Claim 7:
delete "—$CH_2)_m$—$(C(CH_3)_2)_p$—$(CH_2)_n$-$T_2$-$T_3$" and insert -- —$(CH_2)_m$—$(C(CH_3)_2)_p$—$(CH_2)_n$-$T_2$-$T_3$ --

Column 50, lines 11-12, Claim 7:
delete "SO—. SO—" and insert -- $SO_2$, $SO_3$ --

Column 50, line 13, Claim 7:
delete "resent" and insert -- present --

Column 50, lines 20-21, Claim 7:
delete "—$CH_2)_m$—$(C(CH_3)_2)_p$—$(CH_2)_n$-$T_2$-$T_3$" and insert -- —$(CH_2)_m$—$(C(CH_3)_2)_p$—$(CH_2)_n$-$T_2$-$T_3$ --

Column 50, line 23, Claim 7:
after "6" insert -- ; --

Column 50, lines 28-29, Claim 7:
delete "1- or 2-qlycerol, 1- or 2-cyclic qlycerol" and insert -- 1- or 2-glycerol, 1- or 2-cyclic glycerol --

Column 50, line 40, Claim 7:
delete "$CH_2CH_2CH_2OH$, and CH2CH2OCH3" and insert -- $CH_2CH_2F$, $CH_2CH_2OH$, and $CH_2CH_2OCH_3$ --

Column 51, line 19, Claim 15:
delete "$R^a$" and insert -- $R_a$ --

Column 51, line 25, Claim 15:
delete "$R^a$" and insert -- $R_a$ --

Column 52, line 12, Claim 17:
delete "$R^a$" and insert -- $R_a$ --